US011793857B2

(12) United States Patent
Kumagai et al.

(10) Patent No.: US 11,793,857 B2
(45) Date of Patent: *Oct. 24, 2023

(54) HARD TISSUE THERAPEUTICS

(71) Applicant: ORTHOTROPHIX, INC., Oakland, CA (US)

(72) Inventors: Yoshinari Kumagai, Foster City, CA (US); Dawn McGuire, Orinda, CA (US); Meghan Miller, Antioch, CA (US); David Rosen, New Braunfels, CA (US)

(73) Assignee: ORTHOTROPHIX, INC., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/477,918

(22) Filed: Sep. 17, 2021

(65) Prior Publication Data

US 2022/0105154 A1 Apr. 7, 2022

Related U.S. Application Data

(60) Provisional application No. 63/239,791, filed on Sep. 1, 2021, provisional application No. 63/239,793, filed on Sep. 1, 2021, provisional application No. 63/219,060, filed on Jul. 7, 2021, provisional application No. 63/086,334, filed on Oct. 1, 2020.

(51) Int. Cl.
| | | |
|---|---|---|
| *A61K 38/00* | (2006.01) | |
| *A61K 38/16* | (2006.01) | |
| *A61K 9/00* | (2006.01) | |
| *A61P 19/02* | (2006.01) | |
| *A61B 5/00* | (2006.01) | |
| *A61B 5/055* | (2006.01) | |
| *A61B 6/03* | (2006.01) | |
| *A61B 6/00* | (2006.01) | |
| *A61B 8/08* | (2006.01) | |
| *A61K 38/18* | (2006.01) | |

(52) U.S. Cl.
CPC ............. *A61K 38/16* (2013.01); *A61B 5/055* (2013.01); *A61B 5/4504* (2013.01); *A61B 5/4848* (2013.01); *A61B 6/032* (2013.01); *A61B 6/505* (2013.01); *A61B 8/0875* (2013.01); *A61K 9/0019* (2013.01); *A61K 38/18* (2013.01); *A61P 19/02* (2018.01)

(58) Field of Classification Search
CPC ...... A61K 38/16; A61K 9/0019; A61K 38/18; A61P 19/02; A61B 5/055; A61B 5/4504; A61B 5/4848; A61B 6/032; A61B 6/505; A61B 8/0875

See application file for complete search history.

(56) References Cited

U.S. PATENT DOCUMENTS

| | | |
|---|---|---|
| 7,638,486 B2 | 12/2009 | Lazarov et al. |
| 7,888,462 B2 | 2/2011 | Middleton-Hardie |
| 8,426,558 B2 * | 4/2013 | Middleton-Hardie ...................... A61P 29/00 |
| | | 530/324 |
| 8,426,588 B2 | 4/2013 | Makino |
| 11,278,413 B1 | 3/2022 | Lang |
| 2002/0147392 A1 | 10/2002 | Steines et al. |
| 2008/0096798 A1 | 4/2008 | Lazarov et al. |
| 2009/0062201 A1 | 3/2009 | Kumagai et al. |
| 2011/0105401 A1 | 5/2011 | Middleton-Hardie et al. |
| 2011/0266265 A1 | 11/2011 | Lang |
| 2019/0388503 A1 | 12/2019 | Kumagai et al. |
| 2020/0002393 A1 | 1/2020 | Kumagai et al. |
| 2020/0009220 A1 | 1/2020 | Kumagai |
| 2020/0129588 A1 * | 4/2020 | Kumagai ........... A61K 38/1709 |
| 2020/0170939 A1 * | 6/2020 | Kumagai ........... A61K 38/1709 |
| 2022/0133484 A1 | 5/2022 | Lang |

FOREIGN PATENT DOCUMENTS

| | | | |
|---|---|---|---|
| WO | WO 2008/091632 | 7/2008 | |
| WO | WO-2020117360 A1 * | 6/2020 | ........... A61B 17/562 |

OTHER PUBLICATIONS

Christensen et al. (JBMR Plus, 2020, vol. 4(8), pp. 1-8). (Year: 2020).*
Li et al. (Arthritis Res. Ther., 2013, vol. 15(6), article 223). (Year: 2013).*
Neogi et al in "MRI-based three-dimensional bone shape of the knee predicts onset of knee osteoarthritis: Data from the Osteoarthritis Initiative" (Arthritis Rheum 2013 vol. 65, No. 8, pp. 2048-2058). (Year: 2013).*
Perry et al "Measurement of synovial tissue volume in knee osteoarthritis using a semiautomated MRI-based quantitative approach" (Magn Reson Med 2019: vol. 81: pp. 3056-3064). (Year: 2019).*
Orthotrophix (Aug. 15, 2013). (Year: 2013).*
Hu & Collins (NeuroImage vol. 36, 2007: pp. 672-683). (Year: 2007).*
McGuire (Abstracts for Osteoarthritis and Cartilage vol. 26: 2018: #463). (Year: 2018).*
McGuire (Arthritis Research & Therapy; 2021, vol. 23: pp. 1-9). (Year: 2021).*
Ortho Trophix reference Aug. 15, 2013 (Year: 2013).*
McGuire 2018 Report 463 (Year: 2018).*
McGuire 2021 Arthritis Research & Therapy (Year: 2021).*
Karsdal et al., "Disease-modifying treatments for osteoarthritis (DMOADs) of the knee and hip: lessons learned from failures and opportunities for the future" Osteoarthritis and Cartilage (2016) 24(12)2013-2021.

(Continued)

*Primary Examiner* — Catherine S Hibbert
(74) *Attorney, Agent, or Firm* — Karl Bozicevic; Bozicevic, Field & Francis LLP

(57) ABSTRACT

Compounds, pharmaceutical compositions, and a method of treating hard tissue diseases and disorders are disclosed. The compounds may be a peptide and is structured to bind integrin $\alpha_v\beta_3$ expressed by osteocytes and by selective binding to the cell surface integrin on hard tissue forming cells regulate three-dimensional bone shape, cartilage formation and repair.

15 Claims, 8 Drawing Sheets

Specification includes a Sequence Listing.

(56) References Cited

OTHER PUBLICATIONS

McGuire et al., "TPX-100 Leads to the Marked, Sustained Improvements in Subjects with Kneww Osteoarthritis: Pre-Clinical Rationale and Results of a Controlled Clinical Trial" Osteoarthritis and Cartilage (2018) 26(1):5243.
Walsh et al., "Treating People With Joint Pain" International Association for the Study of Pain (2016) pp. 1-4.
"Cartilage Protection and Formation Have Failed to Move DMOAD Development Forward" OrthoTrophix, 1 page (2021).
"Guidance for Industry, Clinical Development Programs for Drugs, Devices, and Biological Products Intended for the Treatment of Osteoarthritis (OA)" U.S. Department of Health and Human Services, Food and Drug Administration, Center for Drug Evaluation and Research (CDER), Center for Biologics Evaluation and Research (CBER), Center for Device and Radiological Health (CDRH) (Jul. 1999) 12 pages.
Hochberg, et al., "Efficacy and Safety of Intra-Articular Sprifermin in Symptomatic Radiographic Knee Osteoarthritis: Results of the 2-Year Primary Analysis from a 5-Year Randomised, Placebo-Controlled, Phase II Study" 2017 ACR/ARHP Annual Meeting (Oct. 19, 2017) Abstract No. 1L, 4 pages.
Hochberg, et al., "Efficacy and Safety of Intra-articular Sprifermin in Symptomatic Radiographic Knee Osteoarthritis: Pre-specified Analysis of 3-Year Data from a 5-Year Randomized, Placebo-Cotnrolled, Phase II Study" Osteoarthritis and Cartilage (2018) 26:S26-S27) Abstract No. 32.
"Osteoarthritis: Structural Endpoints for the Developments of Drugs, Devices, and Biological Products for Treatment, Guidance for Industry" U.S. Department of Health and Human Services, Food and Drug Administration, Center for Drug Evaluation and Research (CDER), Center for Biologics Evaluation and Research (CBER), Center for Device and Radiological Health (CDRH) (Aug. 2018) 6 pages.
"Patella Cartilage Thickness Change from Baseline" and "Tibiofemoral Cartilage Thickness Change from Baseline" OrthoTrophix (2021). AC-100 from https://www.drubank.ca.drugs/DB05671, pp. 1-3. Accessed Apr. 4, 2020 (Year 2020).
Bork, "Powers and Pitfalls in Sequence Analysis: The 70% Hurdle." Genome Research 10:398-400 (2000).
Bowie et al., "Deciphering the Message in Protein Sequences: Tolerance to Amino Acid Substitutions" Science, 247:1306-1310 (1990).
Burgess et al, "Possible Dissociation of the Heparin-binding and Mitogenic Activities of Heparin-binding (Acidic Fibroblast) Growth Factor-1 from Its Receptor-binding Activities by Site-Directed Mutagenesis of a Single Lysine Residue" J. Cell Biol. 111:2129-2138, 1990.
Christensen et al., "FAM20C-Mediated Phosphorylation of MEPE and Its Acidic Serine- and Aspartate-Rich Motif" JBMRPlus (WOA) 4(8):1-8 (Aug. 2020).

Knee Injury and Osteoarthritis Outcome Score from https://www.physio-pedia.com/KneePInjury_Osteoarthritis_Outcome_Score, pp. 1-8. Accessed Mar. 29, 2020 (Year 2020).
Lazar et al., "Transforming Growth Factor ox: Mutation of Aspartic Acid 47 and Leucine 48 Results in Different Biological Activities" Mol. Cell Biol., 8:1247-1252 (1988).
Li et al., "Subchondral bone in osteoarthritis: insight into risk factors and microstructural changes" Arthritis Research & Therapy, 15:233, pp. 1-12 (2013).
Maheswaran et al. "A Study to Investigate the Osteogenic Potential of Peptide AC-100," EC Orthopaedics, Jan. 31, 2017 (Jan. 31, 2017), vol. 5, Iss. 3, pp. 82-87.
Roemer et al. "An illustrative overview of semi-quantitative MRI scoring of knee osteoarthritis: lessons learned from longitudinal observational studies" Osteoarthritis and Cartilage 24:274e289 275 (2016) (Year: 2016).
Rowe et al. "MEPE has the properties of an osteoblastic phosphatonin and minhibin," Bone, Nov. 26, 2003 (Nov. 26, 2003), vol. 34, Iss. 2, pp. 303-319.
Vincent, G. et al. "Fully Automatic Segmentation of the Knee Joint using Active Appearance Models. Medical Image Analysis for the Clinic: A Grand Challenge." Webpage [online]. Dec. 2009, (p. 1-7).
WOMAC Osteoarthritis Index from https://www.physio-pedia.com/WOMAC_Osteoarthritis_Index, pp. 1-6. Accessed Mar. 29, 2020 (Year: 2020).
Sayre et al., Plos One, May 4, 2017, 12(5):e0176833.
McGuire et al. "Significant, Sustained Improvement in Knee Function after Intra-Articular TPX-100: A Double-Blind, Randomized, Multi-Center, Placebo-Controlled Phase 2 Trail." 2017 ACR Poster.
McGuire et al. "TPX-100 Leads to Marked, Sustained improvements in Subjects with Knee Osteoarthritis: Pre-Clinical Rationale and Results of a Controlled Clinical Trial" 2018 OARSI Poster.
McGuire et al. "Improved Knee Physical Function Correlates Significant with TF Cartilage Thickness Increase after IA TPX-100: Results of a Post Hoc Analysis" 2019 EULAR Abstract.
McGuire et al. "Improved Knee Physical Function Correlates Significantly with TF Cartilage Thickness after IA TPX-100: Results of a Post Hoc Analysis" 2019 EULAR Poster.
McGuire et al. "Study TPX-100-5: Intra-articular TPX-100 Significantly Delays Pathological Bone Shape Change at 6 and 12 Months in Moderate and Sever Tibiofemoral OA" 2019 ACR Bone Shape Poster.
McGuire et al. "Stabilization of Patellar Bone-Shape Correlates Significantly with Reduced Knee Pain Frequency After IA TPX-100 in Subjects with Bilateral Patellofemoral OA" 2019 ACR Pain Abstract.
McGuire et al. "Stabilization of Patellar Bone-Shape Correlates Significantly with Reduced Knee Pain Frequency after IA TPX-100 in Subjects with Bilateral Patellofemoral OA" 2019 ACR Pain Poster.
McGuire et al. "Study TPX-100-5: Intra-Articular TPX-100 Significantly Delays Pathological Bone Shape Change and Stabilizes Cartilage in Moderate to Sever Bilateral Knee OA" 2021 ART Paper.

* cited by examiner

SEQUENCE LISTING

```
<160> NUMBER OF SEQ ID NOS: 16

<210> SEQ ID NO 1
<211> LENGTH: 20
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (3)..(4)
<223> OTHER INFORMATION: Xaa is any amino acid
<220> FEATURE:
<221> NAME/KEY: SITE
<222> LOCATION: (10)..(11)
<223> OTHER INFORMATION: Xaa is any amino acid
<220> FEATURE:
<221> NAME/KEY: SITE
<222> LOCATION: (18)..(19)
<223> OTHER INFORMATION: Xaa is any amino acid

<400> SEQUENCE: 1

Asp Leu Xaa Xaa Arg Gly Asp Asn Asp Xaa Xaa Pro Phe Ser Gly Asp
1               5                   10                  15

Gly Xaa Xaa Phe
            20

<210> SEQ ID NO 2
<211> LENGTH: 20
<212> TYPE: PRT
<213> ORGANISM: Artificial sequence
<220> FEATURE:
<223> OTHER INFORMATION: synthetic sequence

<400> SEQUENCE: 2

Asp Leu Gln Glu Arg Gly Asp Asn Asp Ile Ser Pro Phe Ser Gly Asp
1               5                   10                  15

Gly Gln Pro Phe
            20

<210> SEQ ID NO 3
<211> LENGTH: 20
<212> TYPE: PRT
<213> ORGANISM: Artificial sequence
<220> FEATURE:
<223> OTHER INFORMATION: synthetic sequence

<400> SEQUENCE: 3

Asp Leu Gln Glu Arg Gly Asp Asn Asp Met Ser Pro Phe Ser Gly Asp
1               5                   10                  15

Gly Gln Pro Phe
            20
```

```
<210> SEQ ID NO 4
<211> LENGTH: 20
<212> TYPE: PRT
<213> ORGANISM: Artificial sequence
<220> FEATURE:
<223> OTHER INFORMATION: synthetic sequence

<400> SEQUENCE: 4

Asp Leu Gln Gly Arg Gly Asp Asn Asp Leu Ser Pro Phe Ser Gly Asp
1               5                   10                  15

Gly Pro Pro Phe
            20

<210> SEQ ID NO 5
<211> LENGTH: 20
<212> TYPE: PRT
<213> ORGANISM: Artificial sequence
<220> FEATURE:
<223> OTHER INFORMATION: synthetic sequence

<400> SEQUENCE: 5

Asp Leu Leu Val Arg Gly Asp Asn Asp Val Pro Pro Phe Ser Gly Asp
1               5                   10                  15

Gly Gln His Phe
            20

<210> SEQ ID NO 6
<211> LENGTH: 22
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (3)..(4)
<223> OTHER INFORMATION: Xaa is any amino acid
<220> FEATURE:
<221> NAME/KEY: SITE
<222> LOCATION: (10)..(11)
<223> OTHER INFORMATION: Xaa is any amino acid
<220> FEATURE:
<221> NAME/KEY: SITE
<222> LOCATION: (18)..(19)
<223> OTHER INFORMATION: Xaa is any amino acid

<400> SEQUENCE: 6

Asp Leu Xaa Xaa Arg Gly Asp Asn Asp Xaa Xaa Pro Phe Ser Gly Asp
1               5                   10                  15

Gly Xaa Xaa Phe Lys Asp
            20

<210> SEQ ID NO 7
<211> LENGTH: 22
<212> TYPE: PRT
<213> ORGANISM: Artificial sequence
<220> FEATURE:
<223> OTHER INFORMATION: synthetic sequence

<400> SEQUENCE: 7

Asp Leu Gln Glu Arg Gly Asp Asn Asp Ile Ser Pro Phe Ser Gly Asp
1               5                   10                  15

Gly Gln Pro Phe Lys Asp
            20

<210> SEQ ID NO 8
<211> LENGTH: 22
<212> TYPE: PRT
```

```
<213> ORGANISM: Artificial sequence
<220> FEATURE:
<223> OTHER INFORMATION: synthetic sequence

<400> SEQUENCE: 8

Asp Leu Gln Glu Arg Gly Asp Asn Asp Met Ser Pro Phe Ser Gly Asp
1               5                   10                  15

Gly Gln Pro Phe Lys Asp
            20

<210> SEQ ID NO 9
<211> LENGTH: 22
<212> TYPE: PRT
<213> ORGANISM: Artificial sequence
<220> FEATURE:
<223> OTHER INFORMATION: synthetic sequence

<400> SEQUENCE: 9

Asp Leu Gln Gly Arg Gly Asp Asn Asp Leu Ser Pro Phe Ser Gly Asp
1               5                   10                  15

Gly Pro Pro Phe Lys Asp
            20

<210> SEQ ID NO 10
<211> LENGTH: 23
<212> TYPE: PRT
<213> ORGANISM: Artificial sequence
<220> FEATURE:
<223> OTHER INFORMATION: synthetic sequence

<400> SEQUENCE: 10

Thr Asp Leu Gln Glu Arg Gly Asp Asn Asp Ile Ser Pro Phe Ser Gly
1               5                   10                  15

Asp Gly Gln Pro Phe Lys Asp
            20

<210> SEQ ID NO 11
<211> LENGTH: 23
<212> TYPE: PRT
<213> ORGANISM: Artificial sequence
<220> FEATURE:
<223> OTHER INFORMATION: synthetic sequence

<400> SEQUENCE: 11

Thr Asp Leu Gln Glu Arg Gly Asp Asn Asp Met Ser Pro Phe Ser Gly
1               5                   10                  15

Asp Gly Gln Pro Phe Lys Asp
            20

<210> SEQ ID NO 12
<211> LENGTH: 23
<212> TYPE: PRT
<213> ORGANISM: Artificial sequence
<220> FEATURE:
<223> OTHER INFORMATION: synthetic sequence

<400> SEQUENCE: 12

Pro Asp Leu Gln Glu Arg Gly Asp Asn Asp Ile Ser Pro Phe Ser Gly
1               5                   10                  15

Asp Gly Gln Pro Phe Lys Asp
            20

<210> SEQ ID NO 13
<211> LENGTH: 23
```

```
<212> TYPE: PRT
<213> ORGANISM: Artificial sequence
<220> FEATURE:
<223> OTHER INFORMATION: synthetic sequence

<400> SEQUENCE: 13

Pro Asp Leu Gln Gly Arg Gly Asp Asn Asp Leu Ser Pro Phe Ser Gly
1               5                   10                  15

Asp Gly Pro Pro Phe Lys Asp
            20

<210> SEQ ID NO 14
<211> LENGTH: 23
<212> TYPE: PRT
<213> ORGANISM: Artificial sequence
<220> FEATURE:
<223> OTHER INFORMATION: synthetic sequence

<400> SEQUENCE: 14

Pro Asp Leu Leu Val Arg Gly Asp Asn Asp Val Pro Pro Phe Ser Gly
1               5                   10                  15

Asp Gly Gln His Phe Met His
            20

<210> SEQ ID NO 15
<211> LENGTH: 23
<212> TYPE: PRT
<213> ORGANISM: Artificial sequence
<220> FEATURE:
<223> OTHER INFORMATION: synthetic sequence

<400> SEQUENCE: 15

Gly Phe Gln Asp Ser Leu Asp Ser Asn Arg Gln Asp Pro Gly Thr Asp
1               5                   10                  15

Pro Glu Lys Gly Ile Asp Phe
            20

<210> SEQ ID NO 16
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (3)..(3)
<223> OTHER INFORMATION: The amino acid at position 3 is hydroxyproline

<400> SEQUENCE: 16

Gly Phe Xaa Gly Glu Arg
1               5
```

HARD TISSUE THERAPEUTICS

FIELD OF THE INVENTION

The invention relates to compounds that treat hard tissue diseases and disorders, pharmaceutical compositions containing the compounds, and method of use thereof to treat hard tissue diseases and disorders. More specifically the invention related to such compounds that are peptide which binds integrin $\alpha_v\beta_3$ expressed by osteocytes and are formulated for injection and administered repeatedly over time until the composition delays, arrests, or reverses 3D bone shape change in the patient.

INCORPORATION BY REFERENCE OF SEQUENCE LISTING

A Sequence Listing is provided herewith as a Sequence Listing XML, "BEAR-021_SEQ_LIST_ST25" created on Sep. 30, 2021 and having a size of 6000 bytes. The contents of the Sequence Listing XML are incorporated herein by reference in their entirety.

BACKGROUND

Hard Tissue Formation

Bone, cartilage, and dentin make up the hard tissues of vertebrates.

Hard tissue forming cells differentiate from mesenchymal stem cells (MSCs). Depending on the microenvironments in which they reside, MSCs become committed to specific hard tissue cell lineages and differentiate into those respective lineages. When they commit to the bone lineage, MSCs differentiate into osteoblasts, then further differentiate into mature osteocytes. When they commit to the cartilage lineage, they differentiate into chondroprogenitor cells or chondroblasts, then further differentiate into mature chondrocytes. In a joint, synoviocytes (or synovial cells) can migrate from the synovial membrane to articular cartilage and differentiate into chondrocyte lineage cells in that microenvironment.

When osteoblastic cells are differentiating to become mature osteocytes, they produce biomaterials and enzymes specific to and necessary for bone formation such as type I collagen, osteopontin, osteocalcin, and alkaline phosphatase. Chondroprogenitor cells, in the course of differentiation into chondroblasts and mature chondrocytes, produce cartilage-specific biomaterials including type II collagen and aggrecan. Production of these materials by the respective cell types are upregulated while they are actively differentiating.

Hard Tissue Damages, Diseases, and Disorders

Hard tissue diseases and disorders often seriously limit the physical mobility of patients, which leads to a poor quality of life and a sedentary lifestyle. This can increase the risk for comorbid conditions such as obesity, diabetes, cardiovascular disease, and dementia. Hard tissue diseases and disorders often progress and may never heal. A new therapy that accelerates healing of hard tissues or arrests or delays progression of pathological conditions damaging hard tissues is highly desirable.

Osteoarthritis

Osteoarthritis (OA) is the most common disease of the joints and one of the most widespread of all chronic diseases. In the US, this debilitating condition is second only to heart disease as a cause of work disability in men over 50 years of age. Globally, osteoarthritis is the 6th leading cause of years living with disability (Woolf 2003).

Pain is a common symptom in patients with knee OA. Pain typically is treated with non-steroidal anti-inflammatory drugs (NSAIDs). However, further to the initial Boxed Warning and Warnings and Precautions sections of the prescription labels of NSAIDs in 2005, the United States Food and Drug Administration (FDA) in 2015 strengthened the existing label warning that non-aspirin NSAIDs, including over-the-counter products, increase the chance of a heart attack or stroke (FDA Drug Safety Communication: FDA strengthens warning that non-aspirin nonsteroidal anti-inflammatory drugs (NSAIDs) can cause heart attacks or strokes: Jul. 9, 2015).

Intra-articular treatments using corticosteroids or hyaluronic acid products are also used to reduce pain in knee OA. Corticosteroid injections have been implicated in further cartilage degeneration in the knees (McAlindon 2017), making many clinicians reluctant to use this treatment modality. Corticosteroid injections are not recommended by The American Academy of Orthopaedic Surgeons or The American Association of Orthopaedic Surgeons for treatment of knee OA (Recommendation 8 in AAOS Treatment of Osteoarthritis of the Knee—$2^{nd}$ Edition, Evidence-Based Clinical Practice Guideline: Adopted by American Academy of Orthopaedic Surgeons Board of Directors, May 18, 2013).

While hyaluronic acid or "viscosupplementation" products may reduce joint pain for weeks to months in some patients (Cohen 1998), multiple clinical trials have failed to demonstrate a clinically meaningful treatment effect. The American Academy of Orthopaedic Surgeons and American Association of Orthopaedic Surgeons state "We cannot recommend using hyaluronic acid for patients with symptomatic osteoarthritis of the knee." (Recommendation 9 in AAOS Treatment of Osteoarthritis of the Knee—$2^{nd}$ Edition, Evidence-Based Clinical Practice Guideline: Adopted by American Academy of Orthopaedic Surgeons Board of Directors, May 18, 2013).

Surgical therapies are also being employed to treat OA.

Microfracture and abrasion of the bone under the knee cartilage is used to induce formation of fibrocartilage (scar cartilage). However, with microfracture technique, the normal hyaline cartilage structure cannot be restored, and resulting fibrocartilage is less mechanically stable as compared to the normal cartilage (Erggelet 2016).

Osteochondral autograft/allograft transplantation, or OATS procedure, requires two surgeries and treatment failures are common. Additional surgery is sometimes required to manage complications. In addition, patients cannot weight-bear for approximately six weeks after the OATS procedure, making recovery arduous for some.

Autologous chondrocyte implantation (ACI) of products such as Carticel® also requires two surgeries. In the study of more than 150 patients, 49% of patients required repeat surgery for complications (Zaslav 2009). Common complications include delamination, graft failure and disturbed graft fusion (Niemeyer 2008).

When knee joint deterioration is severe, joint replacement surgery may be the only option. Total knee replacement (TKR) is an invasive and expensive procedure with potentially serious morbidity. Total knee replacement (TKR) costs $35,000-70,000 per knee. This does not include costs of post-operative rehabilitation (at least six weeks) and lost productivity. Prosthetic joints have a limited life expectancy and typically must be replaced after 15-20 years; hence TKR may be reserved for older patients. Nevertheless, the average age of the patients who receive TKR has been falling. While the average age in 2000 in the U.S. was 68 years old, it declined to 65.9 years in 2014 (American Academy of Orthopaedic Surgeons 2018). Over 680,000 TKR surgeries were performed in 2014, and approximately 1.28 million TKR surgeries (excluding revision surgeries) will be performed in the U.S. in 2030, per estimates of The American Academy of Orthopaedic Surgeons (American Academy of Orthopaedic Surgeons Research News Mar. 6, 2018).

Osteoarthritis Therapeutics Targeting Cartilage

Enormous efforts have been made to develop OA treatments that slow knee joint degeneration by promoting formation of articular cartilage or by inhibiting cartilage degradation. This approach to disease modification has been based on the hypothesis that articular cartilage degeneration is the primary pathologic mechanism driving knee OA.

Several groups have attempted to develop inhibitors of matrix metalloproteinases (MMPs), which are hypothesized to have a role in cartilage degradation (Krzeski 2007). Others have attempted to inhibit endogenous nitric oxide, which is believed to accelerate cartilage destruction (Hellio le Graverand 2013). Numerous drugs believed to inhibit cartilage degeneration in knee OA have been tested in controlled clinical trials; however, thus far none has demonstrated the efficacy and safety required for regulatory approval.

Growth factors also have been tested for efficacy in cartilage regeneration. Fibroblast Growth Factor-18 (FGF-18, a.k.a., Sprifermin) was associated with a small but statistically significant increase in tibiofemoral cartilage thickness in subjects with knee OA; however, FGF-18-treated subjects had no significant improvement in clinical outcomes such as knee function or pain when compared with placebo-exposed subjects (Hochberg 2017, Hochberg 2018).

Emphasis on Patient Benefits in New Regulatory Guidance for OA Therapies

The FDA has noted the lack of concordance between structural (cartilage) thickness increase, as measured by MRI or x-ray imaging, and clinical benefits in patients with knee OA. Noting the observed discordance between structural cartilage measures and clinical outcomes, the FDA replaced previous (1999) draft guidance for development of disease-modifying OA drugs (DMOADs) in August 2018.

In the 1999 draft guidance, an increase in joint space width or a delay in narrowing of the joint space as measured by X-ray represented a potentially acceptable endpoint for drug approval.

In the new draft guidance, the FDA offered no specific structural outcome measures or modalities that might be acceptable for DMOAD approval; rather, the Agency emphasized that a treatment must demonstrate meaningful patient benefits, such as improvement of knee pain and/or function, or avoidance or delay in the need for joint replacement surgery, in order to be considered for approval as a DMOAD. Improvements in structural outcomes should be concordant with clinical benefits (Osteoarthritis: Structural Endpoints for Development of Drugs, Devices, and Biological Products for Treatment. Guidance for Industry. FDA 2018).

Three-Dimensional (3D) Subchondral Bone Shape, a New Structural Marker for Knee OA Pathological changes in the bones underlying and supporting knee cartilage have been shown to predict the onset and progression of knee OA and are measurable on MRI even before cartilage loss (Reichenbach 2008). Bone shape in the knee joint can be measured precisely and objectively in three dimensions using MRI-based images (Bowes 2013, Hunter 2016).

Data from the Osteoarthritis Initiative (OAI), a prospective, observational study of more than 4,700 subjects (more than 9,000 knees) with and without knee OA who were followed for four years or longer demonstrated that the 3D shapes of bones comprising the knee joint change over time. In osteoarthritic knees, the rate of change of 3D bone shape is markedly increased compared to that in non-osteoarthritic knees (Bowes 2019).

Data from the OAI indicate that a flattening of bone shape occurs in the femur, tibia and patella over time, even prior to measurable cartilage loss (Bowes 2013). In subjects with knee OA, radiographically defined as a Kellgren-Lawrence (KL) grades of 2 or greater on X-ray, the rate of bone-shape change is significantly faster than that in subjects without OA (KL grade of 0) (Bowes 2019).

As a structural marker, 3D bone shape change predicts radiographic (X-ray) onset of knee OA (Neogi 2013) and is more sensitive to change over time than X-ray (Hunter 2016). The magnitude of 3D bone shape change over the course of four years predicts the likelihood of joint failure as indicated by TKR (Barr 2016), and predicts progression of knee pain better than does semi-quantitative analysis of bone marrow lesions (Dube 2018).

In each of the studies cited, the femur had greater sensitivity to change than did the tibia or patella. The femoral bone shape metric, or "B-score", is a form of statistical z-score that represents where the bone shape lies along a vector from the origin, representing the bone shape of normal (non-osteoarthritic) knees (0) towards the bone shape of osteoarthritic knees (>0, positive direction). Knees used to define the 3D shape vector were categorized using centrally-read and adjudicated Kellgren-Lawrence (KL) grading of X-rays that were obtained as part of the Osteoarthritis Initiative (OAI) (Bowes 2019, Bowes 2020).

The 3D shape change of femur, tibia, and patella bone surfaces can be automatically segmented from MRI images using active appearance models (AAMs) (Williams 2010).

The flattening of the femur, tibia or patella is a component of 3D bone shape change in the knees, which expands the subchondral bone area.

In a nested case-control study from the OAI, changes in bone area and bone shape at 24 months from baseline were measured in subjects with knee OA who were taking bisphosphonates for osteoporosis and in OA-matched non-bisphosphonate users. Subjects in the bisphosphonate group had a statistically significant reduction in bone area expansion in the medial tibia compared with controls (Haj-Mirzaian 2018).

Therapeutic agents such as bisphosphonates used to treat osteoporosis have been investigated in prospective clinical trials in subjects with knee OA.

These include risedronate (Bingham 2006), zolendronate (Laslett 2012), strontium ranelate (Reginster 2013), and calcitonin (Karsdal 2015). Effects on pain have been mixed, with results of the largest study (risedronate; n=2483) favoring placebo over active drug (Bingham 2006). In addition, the potential for serious adverse effects has dampened enthusiasm for these agents. For example, strontium ranelate was found to increase the risk of myocardial infarction and its use has been limited by the European Medicines Agency. None of these drugs has been shown to have a significant effect on the structural progression of OA as measured by X-ray or 3D bone shape analysis.

To date, the only therapeutic agent that has been shown to significantly reduce pathological 3D bone shape change is the peptide of amino acid sequence TDLQERGDNDIS-PFSGDGQPFKD (SEQ ID No: 10) (McGuire 2019, McGuire 2020).

Importantly, in addition to bone shape stabilization in the joint, the peptide of SEQ ID No: 10 has demonstrated clinically meaningful and statistically significant improvements in standardized, validated outcome measures of critical knee functions, sports and recreation activities, knee-related QOL, knee pain frequency, knee pain going up or down stairs, and in the most widely used knee OA outcome measure, the WOMAC total score (McGuire 2017, McGuire 2018).

These observations are remarkable in showing, for the first time, that pathological 3D bone shape change in the knees can be slowed, arrested, or possibly reversed by a drug therapy, and that slowing or arresting pathological 3D bone shape change is linked to significant clinical benefits across a broad range of subjects, including many with severe tibiofemoral knee OA (McGuire 2019).

Another notable result was the significant correlation between reduced 3D bone shape change and increased thickness or stabilization of tibiofemoral cartilage (McGuire 2020). The reduction in rate of pathological bone shape change by the peptide of SEQ ID No: 10 may have stabilized the overlying cartilage by providing better mechanical and trophic support.

In addition, the peptide of SEQ ID No: 10 has been shown in vitro and in vivo to promote chondrocyte differentiation and secretion of critical matrix elements such as type II collagen and aggrecan.

TPX-100 Peptide, Its Orthologues and Analogues

TPX-100 is a synthetic peptide consisting of 23 amino acids with amino acid sequence of TDLQERGDNDIS-PFSGDGQPFKD (SEQ ID No: 10), derived from human Matrix Extracellular Phosphoglycoprotein, or MEPE.

TPX-100 selectively acts on cells committed to hard tissue lineages, i.e., bone, cartilage, and dentin. Results of in vitro and in vivo non-clinical studies, including GLP short- and long-term toxicology studies with systemically or locally administered TPX-100, have never demonstrated biological effects of the peptide on cell types, tissues, or organs other than cartilage, bone, and dentin.

Orthologues of MEPE have been identified in several mammals, and thus, their corresponding TPX-100 orthologues have been identified as well, in chimpanzee, macaque, cow, dog, rat, and mouse. The orthologues share a consensus amino acid sequence: DLXXRGDNDXXPFSGDGXXF (SEQ ID No: 1).

Whereas the least homologous orthologue to human TPX-100 is murine/rat, the human and murine/rat orthologues demonstrated the same biological activities on human and rat bone cells interchangeably (Nagel 2004). The human orthologue, TPX-100, has exhibited activities on bone, cartilage, and dentin in mouse, rat, dog, goat, and baboon (Hayashibara 2004, Lazarov 2004, Rosen 2006, Six 2007, Middleton-Hardie 2010, U.S. Pat. Nos. 7,888,462 and 8,426, 558). It is therefore reasonably assumed that the peptides sharing the consensus amino acid sequence of SEQ ID No: 1 share the biological activities in hard tissues. TPX-100 has been administered in vivo studies systemically or locally by conventional methods via intravenous, subcutaneous, intracutaneous, intra-articular or other routes.

Hard Tissue Maintenance and Homeostasis

Hard tissue cells and constituents consistently turn over. Old tissues are replaced with newly formed ones to maintain and/or strengthen their biological function.

A long-term understanding of bone homeostasis is that new bone tissues are consistently formed by osteoblasts and old bone tissues are consistently degraded by osteoclastic bone resorption. The current therapeutic agents used to treat osteoporosis and other bone disorders were developed based on this understanding. They target the reduction of excessive bone resorption or the promotion of bone formation.

In recent years, the activities and secretions of mature osteocytes have been studied as a possible additional mechanism of healthy bone remodeling and homeostasis. In healthy bone, osteocytes are connected to each other within the bone matrix. Osteocytes send out long dendritic processes (the dendrites) through channels within the bone matrix (canaliculi). This dendritic network connecting these osteocytes with each other and with osteoblasts and osteoclasts. Osteocytes produce multiple enzymes such as matrix metalloproteinases (MMPs), carbonic anhydrase, and cathepsin K, which are thought to play important roles in healthy bone remodeling and homeostasis.

In healthy bone tissue, osteocytes are well connected to each other via canaliculi. Type I collagen, the most abundant extracellular matrix (ECM) molecule in bone tissue, is organized into 3-dimensional structures consisting of fibrils and larger fibers. This type of organization is important for maintaining bone strength and resilience.

In the bones of aged animals or those with disrupted bone homeostasis (e.g., osteoarthritic subchondral bone), both the length and number of osteocyte canaliculi are reduced. In addition, the expression of several important enzymes is significantly reduced, and type I collagen in the bone tissue is less organized. As a result, the mineral content of the bone can become elevated resulting in sclerotic bone (Mazur 2019).

To date, there is no approved therapeutic agent targeting these osteocyte-mediated homeostasis mechanisms in bone.

Articular cartilage has a limited ability to repair itself, primarily due to a lack of neurovascular supply. However, it is believed to be capable of some remodeling. Articular cartilage consists primarily of chondrocytes, ECMs, and water. The key ECMs that maintain the structure and resilience of articular cartilage are type II collagen and the cartilage specific proteoglycan, aggrecan. The glycosaminoglycan chains on this proteoglycan are highly hydrated, which plays a critical role in the resilience of cartilage. Approximately 70-80% of articular cartilage is water. Type II collagen and aggrecan are produced by cells of the chondrocyte lineage. Chondrocyte lineage cells also produce MMPs, which are thought to be responsible for degradation of the ECMs of cartilage. There has been no approved therapeutic drug, which targets cartilage formation, degradation, or homeostasis.

TGF-β Signaling in Bone and Cartilage Cells

It has been known that proliferation and/or differentiation of bone and cartilage cells are stimulated by growth factors. In particular, molecules that belong to transforming growth factor-β (TGF-β) superfamily are known to promote proliferation and/or differentiation of osteoblastic and chondroprogenitor cells. TGF-β is ubiquitous in most part of the body including in the hard tissue microenvironment.

Osteoblasts express type I and type II TGF-β receptors on their surfaces. Each of them is a homodimer, and the type I and type II receptors are separated on the cell surface while the cells are quiescent. Once TGF-β binds the type II TGF-β receptor, the ligand-receptor complex assembles with the type I TGF-β receptor, forming an active TGF-β receptor complex. The activated TGF-β receptor complex phosphorylates effectors, such as Smad2/3, thereby activating them.

The activated Smad2/3 are translocated to the nucleus, bind with a transcription factor Runx2, and trigger gene transcription of leading to production of molecules needed for bone formation, such as type I collagen, osteopontin, osteocalcin and others (Wu 2016).

Type I and type II TGF-β receptors are also expressed on chondroprogenitor cells, where they can form active TGF-β receptor complexes leading to Smad2/3 activation. Activated Smad2/3 are translocated to the nucleus bind a transcription factor Sox9, and trigger transcription of the genes of the ECMs necessary to form articular cartilage. At the same time, the activated Smad2/3 also bind another transcription factor, Runx2, which turns off transcription of cartilage degradation enzymes such as MMPs (Cooke 2011). The role of the transcription factor Runx2 in chondroblasts is different from its role in osteoblasts.

Recent research also has demonstrated that TGF-β signaling plays an important role in osteocyte regulation of bone homeostasis. Activation of Smad2/3 by the TGF-β receptor complex on osteocytes promotes expression of MMP-13 and other enzymes essential for bone homeostasis, as well as extension and elongation of canaliculi.

In summary, TGF-β signaling plays critical roles in osteoblastic bone formation, chondroblastic cartilage formation, and bone homeostasis regulated by osteocytes.

Stimulation of the TGF-β signaling system may treat hard tissue diseases and disorders. However, exogenously administered TGF-β is known to generate adverse events such as tissue fibrosis (Biemacka 2011). Stimulation of the effectors in the TGF-β signaling cascade by an exogenously administered compound is also unrealistic, as the same effectors are used by other cell types as well, leading to adverse off target effects.

To overcome these hurdles, target delivery of TGF-β is being attempted using chondrocytes transfected with TGF-β1 gene and implanting them into the knee joint. Even if this method shows a promise, it involves potential risks typical to cell therapies experienced in autologous chondrocyte transplantation and a high cost (Guermazi 2017, Lee 2020)

In the hard tissue microenvironment, it is believed that a biologically inactive (latent) form of TGF-β is retained in the ECMs, creating a reservoir of endogenous TGF-β that can be released to act on hard tissue cells.

If TGF-β signaling in the desired hard tissue cells (i.e., osteocytes, osteoblasts, and/or chondrocytes) can be selectively activated without affecting other cell types or tissues, it would be a useful approach to treating hard tissue diseases and disorders.

Because TGF-β is ubiquitous exists in the body, including in the microenvironments of hard tissues, a key question is how TGF-β can be stimulated selectively in target hard tissue cells.

Integrins

Integrins are a group of molecules expressed on cell surface of many cell types. They are made from two subunits, alpha (a) and beta (p). Integrins are often described as being cell adhesion receptors and play many important roles in the normal development as well as in pathological conditions.

To date, 24 integrins have been identified. Integrins can be broadly categorized into several groups. Of the 24 known integrins, 8 binds to the tripeptide sequence RGD (Arg-Gly-Asp). Others bind various collagens and other ECM proteins such as laminin.

The collagen-binding integrins include the $\alpha_1\beta_1$, $\alpha_2\beta_1$, $\alpha_{10}\beta_1$, and $\alpha_{11}\beta_1$ forms and recognize a different amino acid motif found in triple helical collagens—GFOGER (Gly-Phe-Hyp-Gly-Glu-Arg).

Integrins are widely distributed on most cell types. Each cell type has its own set of integrins, which can vary depending on the local environment. Table 1 (adapted from Barczyk 2010) shows a list of all 24 known integrins, their recognition sequences, and their major ligands.

TABLE 1

Integrins, Their Expressing Cells, and Binding Types

| Integrin | Human α Chain Characteristics | Prototypic Ligands/recognition sequences |
|---|---|---|
| α1β1 (CD49a, VLA1) | 1151 aa | collagens (collagen IV > collagen I (GFOGER); collagen IX) |
| α2β1 (CD49b, VLA2) | 1181 aa | collagens (collagen I > collagen IV GFOGER); collagen IX) |
| α3β1 (CD49c, VLA3) | 1050 aa, splice variants α3 A and α3B | laminins (LN-511 > LN-322 > LN-211) |
| α4β1 (CD49d, VLA4) | 10038 aa | fibronectin VICAM-1 |
| α5β1 (CD49d, VLA4) | 1049 aa | fibronectin (RGD) |
| α6β1 (CD49d, VLA6) | 1073 aa, splice variants α5A and α6B | laminins (LN-511 > LN-211 > LN-411 > LN-111) |
| α7β1 | 1137 aa, splice variants, XI, X2 α7A, α7B | α7X1p1: laminins (LN-511 > LN-211 > LN-411 > LN-111) |
| α8β1 | 1025 aa | fibronectin, vitronectin, nephronectin (RGD) |
| α9β1 | 1053 aa | tenascin-C, VEGF-C, VEGF-D |
| α10β1 | 1167 aa | collagens (collagen IV > collagen VI > collagen II (GFOGER); collage IX) |
| α11β1 | 1188 aa, inserted domain 21 aa | collagens (collagen I > collagen IV > (GFOGER); collagen IX) |
| αLβ2 (CD11a) | 1170 aa | ICAM-1, -2, -3, -5 |
| αMβ2 (CD11b) | 1153 aa | iC3b, fibrinogen + more |
| αXβ2 (CD11c) | 1163 aa | iC3b, fibrinogen + more |
| αDβ2 (CD11d) | 1162 aa | ICAM-3, VCAM-1 |
| αIIBβ3 (CD41, GpIIb) | 1039 aa | fribinogen, fibronectin (RGD) |
| α6β4 | | laminins (LN-332, LN-511) |
| αvβ1 (CD51) | 1048 aa | fibronectin, vitronectin (RGD) |
| αvβ3 | | vitronectin, fibronectin, fibrinogen (ROD) |
| αvβ5 | | vitronectin (RGD) |
| αvβ6 | | fibronectin, TGF-β-LAP (RGD) |
| αvβ8 | | vitronectin, TGF-β-LAP (RGD) |
| αEβ7 (CD103, HML-1) | 1178 aa | E-cadherin |
| α4β7 | | MadCAM-1, fibronectin, VCAM-1 |

Cell surface integrins bind their respective ligands or binding partners and such bindings are believed to regulate specific functions in, and/or responses by, the cells. Many integrins bind several molecules found on multiple cell types with different recognition sequences (e.g., collagen and RGD, etc.) (Barczyk 2010; Marie 2020).

Integrins have been targets for novel therapeutic agents in several areas. In cancer treatment, for example, blocking agents targeting specific integrins involved in tumor angiogenesis and metastatic spread of cancer have been used in clinical trials of malignant melanoma (Huang 2018).

Integrins on Hard Tissue Cells

Several integrins are expressed on cells in the cartilage and bone lineage (Loeser, 2014; Marie 2020). The functions of these integrins in bone and cartilage biology are not well understood, although there are a number of emerging hypotheses.

One function that has been characterized involves the role of integrins in promoting cell attachment to the extracellular matrix. This occurs with cells in the bone and cartilage cell lineage. Integrin binding may also trigger proliferation and/or differentiation of bone and cartilage cells. For example, $\alpha_2\beta_1$, integrin on osteoblasts binds type I collagen, and $\alpha_{10}\beta_1$ on chondroblasts or chondroprogenitor cells binds types II and VI collagen. Many integrins bind fibronectin ($\alpha_5\beta_1$ and $\alpha_v\beta_1$, for example). Other integrins bind extracellular matrix molecules such as laminin and the latency associated peptide (LAP) for TGF-β. A number of ECMs and/or fragments of these ECMs have been investigated as potential therapeutics. However, to date, none have been successfully developed.

It has recently been shown that integrins $\alpha_v\beta_6$ and $\alpha_v\beta_8$ are involved in converting latent (inactive) TGF-β held in the ECMs into its active form (Wipff, 2008), thus enabling TGF-β to signal through its receptor complex. This activation is believed to occur via proteolytic cleavage of the TGF-β LAP to release active TGF-β. These $\alpha_v\beta_6$ and $\alpha_v\beta_8$ integrins are therefore thought to play an important role in bone and cartilage biology by helping to modulate the local levels of endogenous active TGF-β.

It has also been hypothesized that specific integrins expressed by hard tissue cells interact with the surrounding ECMs and the cytoskeleton to enable bone remodeling via TGF-β (Rys 2015, Rys 2016). This signaling, in response to a mechanical load, is thought to occur through assembly of TGF-β type I and type II receptors to form the active receptor complex.

Integrin $\alpha_v\beta_3$

Integrin $\alpha_v\beta_3$ has been identified on a variety of cell types with many proposed functions. Due to its presence on vascular cells, targeting $\alpha_v\beta_3$ has been proposed as an approach to blocking tumor metastasis (Huang 2018, Alday-Parejo 2019).

Integrin $\alpha_v\beta_3$ has been studied extensively in relation to bone biology. Early studies identified that $\alpha_v\beta_3$ is expressed on osteoclasts, the cells primarily responsible for bone resorption. Ross, et. al. demonstrated the important role of integrin $\alpha_v\beta_3$ in osteoclast attachment to bone matrix and regulation of bone resorption (Ross 1993). Furthermore, it has been shown that small chemical molecules that act as antagonists to $\alpha_v\beta_3$ are able to block bone resorption in vitro (Engleman 1997). Therefore, it was proposed that $\alpha_v\beta_3$ antagonists could be good candidates for the treatment of bone loss conditions such as osteoporosis (Horton 2001, Marie 2013). A phase 2 clinical trial with an $\alpha_v\beta_3$ antagonist (L-0084574) demonstrated an increase bone mineral density (BMD) in both the lumbar spine and hip in postmenopausal women, those most at risk for osteoporosis (Murphy 2005). However, we are not aware of any such compound in process of approved by regulatory agencies. Antibodies to $\alpha_v\beta_3$ have also been investigated as possible therapeutics for a number of conditions (Kok 2002; Borst 2017). Monoclonal antibodies to $\alpha_v\beta_3$ have shown some success in various cancers (Liu 2008). A monoclonal antibody to $\alpha_v\beta_3$ has been shown to block bone resorption in preclinical studies (Gramoun 2007), but there have no reports of successful development of this compound for the treatment of bone diseases.

Integrin $\alpha_v\beta_3$ is also expressed by osteoblasts and osteocytes, although less is known about the role(s) of $\alpha_v\beta_3$ in these cells. In vitro, $\alpha_v\beta_3$ has been shown to inhibit bone mineralization and differentiation by osteoblasts, but also to stimulate osteoblast proliferation (Cheng 2001). Other studies have reported that $\alpha_v\beta_3$ and peptidomimetics promote osteoblast differentiation in vitro (Marie 2013; Fraioli 2015).

Osteoblastic differentiation in vitro by BMP-2 was shown to occur via a $\alpha_v\beta_3$ dependent pathway (Su 2010). Osteocytes can modulate bone homeostasis in part through dendritic mechanosensors. Thi, et. al. demonstrated that this response via mechanosensors requires $\alpha_v\beta_3$ (Thi 2013).

SUMMARY OF THE INVENTION

The invention includes a method of treatment, comprising:
   injecting a patient with a composition comprising a pharmaceutically acceptable, injectable carrier, and a peptide which binds integrin $\alpha_v\beta_3$ expressed by osteocytes, wherein the peptide is agonistic on binding to integrin $\alpha_v\beta_3$ expressed by osteocytes, and is not antagonistic, inhibitory, or blocking whereby binding to integrin $\alpha_v\beta_3$ expressed by osteocytes is at a level so as to result in improving joint function upon injection into the patient.

The invention includes a method of treatment wherein the binding affinity of the peptide to integrin $\alpha_v\beta_3$ is at least 300 times higher than its binding affinity to the integrins $\alpha_v\beta_1$, $\alpha_v\beta_6$, $\alpha_v\beta_8$, $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_8\beta_1$, $\alpha_9\beta_1$, and $\alpha_{10}\beta_1$.

The invention includes a method of treatment wherein the peptide also binds integrin $\alpha_v\beta_5$ with a lower affinity than the peptide's affinity to integrin $\alpha_v\beta_3$.

The invention includes a method of treatment wherein the binding affinity of the peptide to integrin $\alpha_v\beta_3$ is at least three (3) times higher than its binding affinity to the integrin $\alpha_v\beta_5$.

The invention includes a method of treatment wherein the peptide comprises 20 to 50 amino acids, containing a general amino acid sequence of DLXXRGDNDXXPFSGDGXXF (SEQ ID No:1), wherein X is any amino acid.

The invention includes a method of treatment wherein the peptide is a peptide selected from the group consisting of a peptide of SEQ ID No: 2, SEQ ID No: 3, SEQ ID No: 4, and SEQ ID No: 5.

The invention includes a method of treatment wherein the peptide comprises at least 22 amino acids containing a general amino acid sequence of DLXXRGDNDXXPFSGDGXXFKD (SEQ ID No: 6), wherein X is any amino acid.

The invention includes a method of treatment whereby the injecting results in slowing a change of three-dimensional (3D) bone shape upon injection into a subject.

The invention includes a method of treatment further comprising:
   continuing the injecting until the composition delays, arrests, or reverses 3D bone shape change in the patient.

The invention includes a method of treatment wherein the 3D bone shape change occurs in a joint of the patient.

The invention includes a method of treatment wherein the 3D bone shape change occurs in a knee joint.

The invention includes a method of treatment wherein the 3D bone shape change in the joint is associated with natural aging.

The invention includes a method of treatment wherein the 3D bone shape change in the joint is pathological.

The invention includes a method of treatment wherein the 3D bone shape change in the joint is associated with one or more of osteoarthritis, rheumatoid arthritis, trauma, osteoporosis, disc herniation, spinal injury, or temporomandibular disorder.

The invention includes a method of treatment wherein the 3D bone shape change occurs in one or more of the joints of knee, hip, ankle, toe, finger, hand, wrist, elbow, shoulder, spine, or jaw.

The invention includes a method of treatment further comprising:
measuring 3D bone shape change by obtaining a bone image and analyzing the image with an algorithm which calculates the 3D bone shape.

The invention includes a method of treatment wherein the bone image is obtained using imaging technology selected from the group consisting of magnetic resonance (MR), radiography (X-ray), computer tomography (CT) and ultrasound.

The invention includes a method of treatment wherein the algorithm is based on active appearance modeling (AAM).

The invention includes a method of treatment wherein the 3D bone shape is determined by z-score where an average healthy 3D bone shape is specified as score of zero (0).

The invention includes a method of treatment wherein the 3D bone shape is determined by B-score.

The invention includes a method of treatment wherein the composition reduces excessive mineralization of the bone.

The invention includes a method of treatment wherein the composition reduces excessive bone sclerosis.

The invention includes a method of treatment wherein the pharmaceutical composition accelerates healing of bone fracture in the patient.

The invention includes a method of treatment wherein the bone fracture is caused by osteoporosis, osteoarthritis, rheumatoid arthritis, trauma, osteoporosis, disc herniation, and/or spinal injury.

The invention includes a method of treatment wherein the bone fracture healing is monitored by obtaining the bone image using any one of magnetic resonance (MR), radiography (X-ray), computer tomography (CT) or ultrasound.

The invention includes a method of treatment further comprising:
obtaining a first image of the bone prior to the administration the pharmaceutical composition;
obtaining a second image of the bone after the administration;
comparing the first image with the second image; and
determining the therapeutic impact of the pharmaceutical composition on the bone.

The invention includes group of compounds that slows the rate of change in three-dimensional (3D) bone shape is presented.

3D bone shape change occurs in any individual in relation to skeletal aging. Accelerated or advanced 3D bone shape change is known to be pathological in joint disorders, particularly in osteoarthritis, and correlates with onset, progression, clinical symptoms, and prognosis in knee OA. Slowing, arresting, or reversing 3D bone shape change in the joint is beneficial in slowing joint degeneration and in treating and/or preventing osteoarthritis and other joint diseases and disorders.

When a compound belonging to this group is used to treat osteoarthritis and/or other joint diseases and disorders including joint trauma, function and/or pain of the joint associated with the joint diseases and disorders are/is improved.

The compounds are characterized by their selective binding to integrin $\alpha_v\beta_3$ expressed by osteocytes. The binding to integrin $\alpha_v\beta_3$ is agonistic and not antagonistic, inhibitory, or blocking.

The binding affinity of the compounds to integrin $\alpha_v\beta_3$ is at least 300 times higher than their binding affinities to other integrins known to be expressed by osteocytes and other hard tissue cells including $\alpha_v\beta_1$, $\alpha_v\beta_6$, $\alpha_v\beta_8$, $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_8\beta_1$, $\alpha_9\beta_1$, and $\alpha_{10}\beta_1$.

The compounds may also bind another osteocyte-expressed integrin, $\alpha_v\beta_5$, but with a lower affinity than that for $\alpha_v\beta_3$.

There is no limitation with regard to the type of the compound as far as it has the binding properties described above. It can be a peptide, protein, glycoprotein, or non-peptide molecule, regardless of its manufacturing method.

A group of peptides within the scope of this invention is presented by a general amino acid sequence of DLXXRGDNDXXPFSGDGXXF (SEQ ID No:1), wherein X is any amino acid. Any peptide with 20-50 amino acids having this general amino acid sequence is within the scope of this invention.

The peptides with following general or specific amino acid sequences are within the scope of this invention. X is any amino acid.

```
                                    (SEQ ID No: 2)
DLQERGDNDISPFSGDGQPF (SEQ ID No: 3)
DLQERGDNDMSPFSGDGQPF (SEQ ID No: 4)
DLQGRGDNDLSPFSGDGPPF (SEQ ID No: 5)
DLLVRGDNDVPPFSGDGQHF (SEQ ID No: 6)
DLXXRGDNDXXPFSGDGXXFKD (SEQ ID No: 7)
DLQERGDNDISPFSGDGQPFKD (SEQ ID No: 8)
DLQERGDNDMSPFSGDGQPFKD (SEQ ID No: 9)
DLQGRGDNDLSPFSGDGPPFKD (SEQ ID No: 10)
TDLQERGDNDISPFSGDGQPFKD (SEQ ID No: 11)
TDLQERGDNDMSPFSGDGQPFKD (SEQ ID No: 12)
PDLQERGDNDISPFSGDGQPFKD (SEQ ID No: 13)
PDLQGRGDNDLSPFSGDGPPFKD (SEQ ID No: 14)
PDLLVRGDNDVPPFSGDGQHFMH
```

Any of the peptide above can be a linear or a cyclic peptide.

The compound with the binding property described above can be an antibody.

The compound can be a non-peptide compound.

A pharmaceutical composition comprising a therapeutically effective amount of any compound described above with a pharmaceutically acceptable carrier is within the scope of this invention.

Another aspect of this invention is a method of impacting bone structure, comprising administration of the pharmaceutical composition described in the preceding paragraph to a patient.

The method delays, arrests, or reverses three-dimensional (3D) bone shape change in the patient.

The method impacts 3D bone shape change in a joint of the patient, in particular, the knee joint.

The 3D bone shape change in the joint treated by this method either can be associated with natural aging or associated with a pathological process.

Pathological 3D bone shape change can be with one or more of osteoarthritis, rheumatoid arthritis, trauma, osteoporosis, spinal injury, disc herniation, or temporomandibular disorder affecting any joint of knee, hip, ankle, finger, hand, wrist, elbow, shoulder, spine, or jaw.

In this method, the 3D bone shape change can be measured by obtaining and segmenting bone images and analyzing them with an algorithm that calculates 3D bone shape.

The bone image can be obtained using one of broadly used imaging methods including but not limited to magnetic resonance (MR), radiography (X-ray), computer tomography (CT) and ultrasound.

An algorithm based on active appearance modeling (AAM) is preferred for the analysis of 3D bone shape change.

The extent of 3D bone shape change can be determined by a z-score, where an average healthy 3D bone shape is specified as a score of zero (0). An example of this scoring is the B-score.

This method also prevents or reduces excessive mineralization and/or sclerosis of the bone in the patient.

Another use of this method is accelerating healing of bone fractures caused by any one or more of osteoporosis, osteoarthritis, rheumatoid arthritis, trauma, spinal injury, and/or disc herniation.

The healing process of the bone fracture can be monitored using conventional imaging methodologies including but not limited to magnetic resonance (MR), radiography (X-ray), computer tomography (CT) and ultrasound.

In any of these methods of impacting bone structure, the method comprises;
1) obtaining a first image of the bone prior to administering the pharmaceutical composition;
2) obtaining a second image of the bone after administration of the pharmaceutical composition;
3) comparing the first image with the second image; and
4) determining the therapeutic impact of the pharmaceutical composition on the bone.

Another aspect of this invention is the group of compounds that reduces the rate of change of 3D bone shape, which also promotes articular cartilage formation or repair in parallel.

Because each of the activities of pathological 3D shape change reduction in subchondral bones and in articular cartilage formation, stabilization and/or repair in the joint is beneficial in treatment of joint diseases and disorders, this group of compounds should be particularly useful.

These compounds are characterized by their selective binding to integrin $\alpha_v\beta_3$ expressed by both osteocytes and chondroblasts or chondroprogenitor cells, slowing changes in 3D bone shape and promoting cartilage formation, stabilization and/or repair in parallel.

A pharmaceutical composition comprising a therapeutically effective amount of any one of these compounds with a pharmaceutically acceptable carrier is within the scope of this invention.

A method to treat a joint disease or disorder comprising administration the pharmaceutical composition to the patient is also within the scope of this invention.

The method is suitable to treat a joint disease or disorder including but not limited to osteoarthritis, rheumatoid arthritis, trauma, osteoporosis, disc herniation, spinal injury, or temporomandibular joint disorder.

The method can be used to treat a joint disease or disorder in one or more of the joints of knee, hip, ankle, finger, hand, wrist, elbow, shoulder, spine, or jaw.

Another group of compounds of this invention are those characterized by their selective binding to integrin $\alpha_v\beta_3$ expressed by chondroblasts or chondroprogenitor cells and promoting cartilage formation in a patient with a joint defect. These compounds do not necessarily act on osteocytes but selectively affect cartilage cells and promote cartilage formation, stabilization and/or repair.

The binding affinity of the compounds to integrin $\alpha_v\beta_3$ is at least 300 times higher than their binding affinity to other integrins known to be expressed by hard tissue cells including $\alpha_v\beta_1$, $\alpha_v\beta_6$, $\alpha_v\beta_8$, $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_8\beta_1$, $\alpha_9\beta_1$, or $\alpha_{10}\beta_1$.

The compounds may also bind $\alpha_v\beta_5$ but with a lower affinity than that for $\alpha_v\beta_3$.

There is no limitation with regard to the type of the compound as far as it has the binding properties described above. It can be any of peptide, protein, glycoprotein, or non-peptide molecule, regardless of its manufacturing method.

A group of peptides within the scope of this invention are presented by a general amino acid sequence of DLXXRGDNDXXPFSGDGXXF (SEQ ID No: 1), wherein X is any amino acid. Any peptide with 20-50 amino acids having this general amino acid sequence is within the scope of this invention.

The peptides of SEQ ID No: 2-14 are within the scope of this invention.

The peptide can be a linear or a cyclic peptide.

The compound can be an antibody.

The compound can be a non-peptide compound.

A pharmaceutical composition comprising therapeutically effective amount of any compound described above and a pharmaceutically acceptable carrier is within the scope of this invention.

Another aspect of this invention is a method to repair a defect in cartilage in a patient, comprising administration to the patient the pharmaceutical composition described in the preceding paragraph.

The method can be also used when the articular cartilage defect was caused by a disease or a condition selected from osteoarthritis, rheumatoid arthritis, trauma, osteoporosis, disc herniation, spinal injury, or temporomandibular disorder.

The repair process of the articular cartilage can be monitored using conventional imaging methodologies including but not limited to magnetic resonance (MR), radiography (X-ray), computer tomography (CT) and ultrasound.

The method can be used to treat a joint disease or disorder in one or more of the joints of knee, hip, ankle, finger, hand, wrist, elbow, shoulder, spine, or jaw.

The method comprises;
1) obtaining a first image of the cartilage in the joint prior to administering the pharmaceutical composition;
2) obtaining a second image of the cartilage of the joint after the pharmaceutical composition;
3) comparing the first image with the second image; and
4) determining the therapeutic impact of the pharmaceutical composition on the cartilage.

Another aspect of this invention is a method to improve function and/or reduce joint pain caused by joint diseases and disorders, by administration of the pharmaceutical composition described above to a patient.

The method improves the function of the joint such as bending, straightening, twisting, and/or rotating.

If the joint suffers from pain, the method reduces frequency and/or intensity of the pain.

The method reduces the joint pain whether it is associated with any activity or no activity.

The function impairment or pain of the joint this method treats can be associated with natural aging and/or pathological process.

The function impairment or pain of the joint can be that associated with one or more of osteoarthritis, rheumatoid arthritis, trauma, osteoporosis, spinal injury, disc herniation, or temporomandibular disorder affecting any joint of knee, hip, ankle, finger, hand, wrist, elbow, shoulder, spine, or jaw.

In this method, the function and pain can be measured by patient reported outcome measures or casual question and answer between a caregiver and a patient.

In this method to improve joint function and/or pain, the method comprises;
1) measuring or identifying joint function impairment and/or pain prior to administering the pharmaceutical composition;
2) measuring or identifying joint function impairment and/or pain after administration of the pharmaceutical composition;
3) comparing the results from the first and the second measurements or identifications; and
4) determining the therapeutic impact of the pharmaceutical composition on the joint function and/or pain.

The joint function and/or pain can be measured using widely accepted patient reported outcome measures such as WOMAC (Western Ontario and McMaster Universities Osteoarthritis Index), KOOS (Knee injury and Osteoarthritis Outcome Score), HOOS (Hip disability and Osteoarthritis Outcome Score), NRS (Numerical Rating Scale), VAS (Visual Analogue Scale), and so forth.

BRIEF DESCRIPTION OF THE DRAWINGS

The invention is best understood from the following detailed description when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Figure 1:
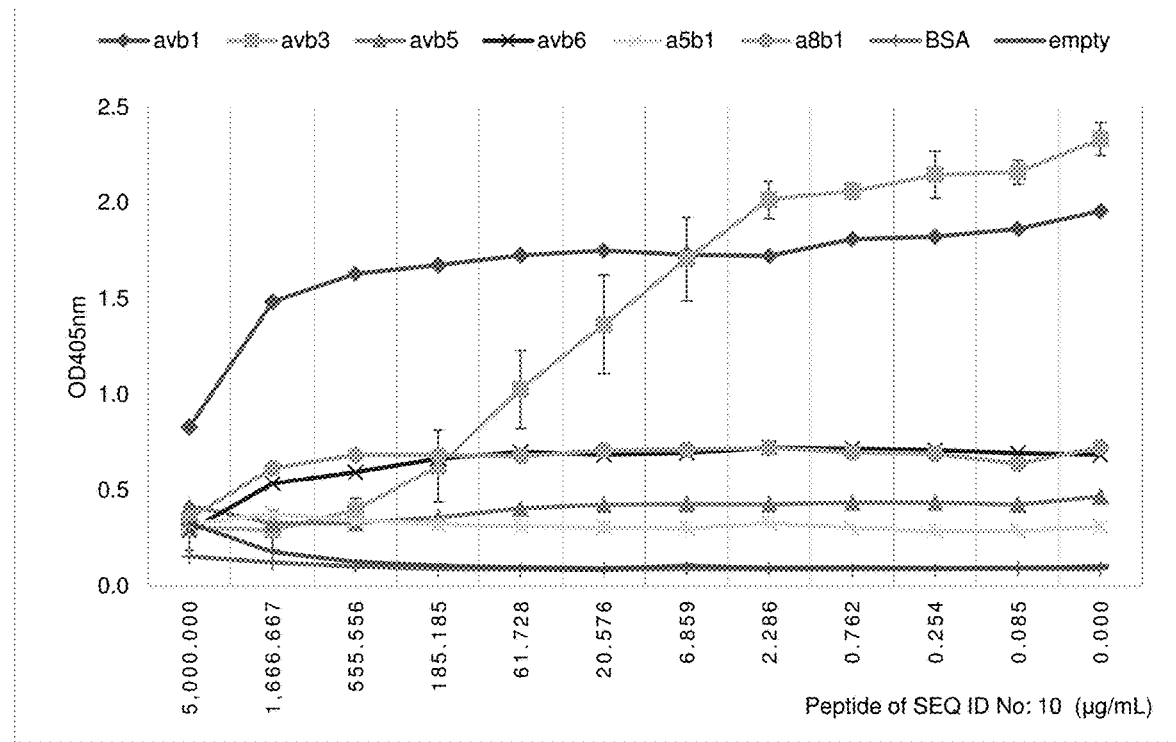
FIG. 1 is a graph showing the results of competitive ELISA (Enzyme-Linked Immuno-Sorbent Assay) with Knottin Peptide comparing the binding of various integrins to the peptide of SEQ ID No: 10. The peptide demonstrated more potent binding to integrin $\alpha_v\beta_3$ than all other integrins.

Before the present methods, uses and formulations are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an injection" includes a plurality of such injections and reference to "the measurement" includes reference to one or more measurements and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Three-Dimensional Bone Shape Change, Joint Function and Joint Pain

As described in the Background section, three-dimensional (3D) shape of the bones, in particular subchondral bones in a joint, show uni-directional change with aging. The rate of change is pathologically advanced and/or accelerated in osteoarthritis (OA), as demonstrated by prospective observational studies with a large database sponsored by the National Institutes of Health, specifically, the Osteoarthritis Initiative (OAI), which includes more than 4700 subjects with and without knee OA who have been followed clinically and radiographically for four years or longer.

In the OAI-based studies, the 3D bone shape change of subchondral bones in the knee joint was demonstrated to effectively distinguish people with OA from those without OA, and reliably predict onset, progression, clinical symptoms, and outcomes, including knee joint failure.

A randomized, double-blind, placebo-controlled clinical trial in subjects with knee OA demonstrated that TPX-100, a fragment peptide of human matrix extracellular phosphoglycoprotein (MEPE), slowed or arrested 3D bone shape change in the OA knee joint compared with placebo controls.

Importantly, the reduced pathological 3D bone shape change also was associated with robust and significant improvements in OA clinical signs and symptoms such as physical function, pain frequency, and multiple other clinical parameters in the knee joint.

Clear associations or statistically significant correlations were observed between reduction in 3D knee joint bone shape changes and clinical benefits.

It was totally unexpected that pathological changes in 3D shape of a bone could be modified by a therapeutic drug. The mechanisms of hard tissue therapeutics conventionally accepted were promotion of hard tissue formation, inhibition of hard tissue degeneration, or combinations thereof.

Another surprise was the association of slowed or arrested 3D shape change in subchondral bones in the knee with improvements in critical knee functions and pain.

The outcomes of the clinical trial led to an invention of a novel treatment method of OA (US Patent Publications:

US-2020-0129588-A1 and US-2020-0170939-A1, as well as a PCT Patent Publication: WO 2020/117360).

Possible Influential Factor on 3D Bone Shape Change

As natural history studies of OA have demonstrated, uni-directional 3D shape change in subchondral bones occurs in all knees in association with aging even in the absence of clinical or radiographic OA. In osteoarthritic knees, 3D shape change is significantly accelerated and advanced as compared to that in non-osteoarthritic knees.

Therefore, it is reasonably assumed that accelerated and/or advanced 3D bone shape change is associated with a deterioration in the knee joint and risk of joint failure.

In addition, 3D bone shape change may be significantly accelerated and advanced by a traumatic event in the joint. Knee joint trauma is associated with an increased risk of knee OA.

Clinical observations indicate that high bone mineral density (BMD) is associated with high prevalence of OA (Nevitt 2010), suggesting that simply increasing bone formation, as with therapies designed to treat osteoporosis that act on osteoblastic bone formation and/or osteoclastic bone resorption, may not necessarily be beneficial to adequate maintenance of 3D bone shape.

In contrast, a role for mature osteocytes residing in the subchondral (periarticular) bones is hypothesized as a key influencer on 3D bone shape maintenance.

Osteocyte Homeostasis and TGF-β Signaling

As introduced in the Background section, it has been shown that the morphology of mature osteocytes is disrupted, and their enzyme production is reduced by aging and by experimental trauma in a joint. These events also were associated with a more disorganized alignment of type I collagen fibers. Type I collagen comprises approximately 90% of the extracellular matrix (ECM) proteins in mature bone. Further, the insufficient production of critical enzymes required for osteocyte homeostasis was associated with increased mineralization and sclerosis of the bone.

These disruptive events in osteocyte homeostasis are thought to be responsible partly or primarily for the progression of 3D bone shape change in aging, trauma, and nontraumatic OA.

Since TGF-β signaling is known to be one of the essential mechanisms for hard tissue cell differentiation and survival, dysregulated and/or insufficient TGF-β signaling is believed to play a role in disrupted osteocyte homeostasis. Also, it has been shown that TGF-β signaling is influenced by interactions between the cell surface integrins on hard tissue cells and surrounding ECMs.

An Integrin That Regulates Osteocyte Homeostasis and 3D Bone Shape Change

TPX-100 and its orthologues have an Arg-Gly-Asp (RGD) sequence, which is a known integrin recognition and binding sequence. Therefore, it was speculated that these peptides could stimulate cell surface integrins on osteocytes, enhance TGF-β signaling in the cells, protect osteocytes from aging-induced or pathological disruption of their healthy homeostasis, and thereby delay or arrest 3D bone shape change associated with aging and/or OA.

Integrins are cell adhesion molecules connecting the cytoskeleton of certain cells with the surrounding ECMs or with other cells. A variety of integrins are known to be expressed by hard tissue cells, including osteocytes. Whereas several integrins are known to bind an RGD sequence, many bind multiple ligands. Therefore, it was difficult to know, a priori, which integrin(s) might be the target of TPX-100 or its analogue molecules.

Thus, integrins known to be expressed by hard tissue cells were tested for their ability to bind TPX-100 and its analogues.

The peptides of SEQ ID No: 10 and 12 (TPX-100 and its canine orthologue), which share common amino acid sequence of SEQ ID No: 1 and 6, and a scrambled peptide of SEQ ID No: 15, were tested for their ability to bind a panel of integrins known to be expressed by one or more hard tissue cells including osteocytes, osteoblasts, and chondroblasts or chondroprogenitor cells. All integrins used in this study contained the human sequence.

This binding study used a molecule that is known to bind many integrins with high affinity, named "Knottin", as a positive control and competitor for binding with the peptides of SEQ ID No: 10, 12, and 15, respectively (Bernhagen, 2017). The binding assay was conducted as a competition ELISA using biotinylated Knottin and unlabeled peptides.

As a result of the binding study using "Knottin," the peptides of SEQ ID No: 10 and 12, respectively, showed selective binding to integrin $\alpha_v\beta_3$ with approximately the same level of binding affinity. The binding affinities to $\alpha_v\beta_3$ were at least 300 times higher than that for other hard tissue expressed integrins: $\alpha_v\beta_1$, $\alpha_v\beta_6$, $\alpha_v\beta_8$, $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_9\beta_1$, or $\alpha_{10}\beta_1$. See EXAMPLE 1. Since higher concentrations of SEQ ID No: 10 and 12 were not used in these studies, it is very possible that the difference in binding affinity is actually much greater than 300 times.

As compared to other integrins: $\alpha_7\beta_1$, $\alpha_8\beta_1$, $\alpha_L\beta_2$, $\alpha_M\beta_2$, $\alpha_X\beta_2$, $\alpha_D\beta_2$, $\alpha_{IIb}\beta_3$, $\alpha_6\beta_4$, $\alpha_E\beta_7$, $\alpha_4\beta_7$, or $\alpha_{11}\beta_1$, the binding affinity of these peptides to integrin $\alpha_v\beta_3$ should be even much higher than 300 times.

There was one notable exception, however. The peptides of SEQ ID No: 10 and 12 did show some binding to $\alpha_v\beta_5$. However, their binding affinities to integrin $\alpha_v\beta_5$ were approximately 3-4 times lower than those for $\alpha_v\beta_3$.

Furthermore, a "scrambled" peptide of SEQ ID No: 15, in which the amino acid sequence was randomly generated and the RGD sequence was disrupted, did not bind any integrins tested (EXAMPLE 1). Collectively, these data indicate that the peptides of SEQ ID No: 10 and 12 selectively bind to integrin $\alpha_v\beta_3$ and require the RGD motif for this binding.

Because the peptides that share a common amino acid sequence of SEQ ID No: 1 show the same hard tissue effects in a cross-species manner as described in the Background, it is believed that the peptides with consensus amino acid sequence of SEQ ID No: 1 selectively bind $\alpha_v\beta_3$ and slow, arrest, or reverse pathological and/or accelerated 3D bone shape change in the joint bones, thereby improve joint function and pain when administered to a joint affected by osteoarthritis, joint trauma, or other joint diseases and disorders.

The peptides of SEQ ID No: 2-14 share the amino acid sequence of SEQ ID No: 1.

Critical Aspects of the Invention

Although the first look of this invention may be a simple connection between a selective integrin binding and biological events, there are some critical points that make this invention meaningful.

First, the highly selective binding to integrin $\alpha_v\beta_3$ is unique in that a hard tissue cell expresses a variety of integrins and several of those integrins share the same subunits, $\alpha_v$ or $\beta_1$. However, the peptide shown to reduce the rate of pathological 3D bone shape change and improve knee function and pain does not bind integrin $\alpha_v\beta_1$. The peptides that regulate 3D bone shape and improve knee function and pain do not bind integrin $\alpha_v\beta$, where $\beta$ can be any $\beta$ subunit other than $\beta_3$ and $\beta_5$, or integrin $\alpha\beta_1$, where α can be any α subunit. It should be noted that an extracellular matrix molecule usually binds multiple integrins and that a peptide having an RGD sequence usually binds multiple integrins. See Table 1.

Second, while there have been a large number of publications addressing the identities, functions, binding types, and binding partners of the integrins expressed by hard tissue cells, the overall conclusion of these publications is that a combination of multiple integrins with multiple binding types and binding partners collectively regulate the overall biological activities of the cell. There have been very few cases that an action on a specific integrin was connected to a specific clinical outcome in human patients.

Third, the clinical outcomes after the use of the selective $\alpha_v\beta_3$ binding molecule have been outstanding. 3D bone shape change is known to occur in all individuals in normal aging and is uni-directional. While the observed clinical benefits associated with a delay in 3D bone shape change was highly unexpected, it was unimagined that such robust clinical efficacy (i.e., significant improvements in joint function and pain) was regulated through a specific integrin.

Fourth, the biological effects and clinical consequences of the compounds of this invention act as agonists of, and signal via, the integrin $\alpha_v\beta_3$. Blocking signaling through integrin $\alpha_v\beta_3$ in order to inhibit biological functions has been the goal of other therapeutic attempts to date. For example, inhibition of integrin $\alpha_v\beta_3$ on osteoclasts was tested as a treatment for osteoporosis in order to block binding of the osteoclast to the bone surface and reduce bone resorption. Attempts to block integrin $\alpha_v\beta_3$-mediated attachment of cancer cells to the endothelium have been used to prevention or reduce cancer metastasis. These studies were all designed to use an antagonist to block signaling through integrin $\alpha_v\beta_3$. Importantly, the compounds of this invention acting as agonists for integrin $\alpha_v\beta_3$, triggering a cascade of cellular events and thereby producing beneficial therapeutic effects.

No inhibition of osteoclastic bone resorption by the peptides of SEQ ID No: 1-14 have been observed to date. No cancer-related effects have been found in any studies involving these molecules. Multiple short and long term GLP toxicology studies have shown no inhibitory activities on any cell types or organs. These observations also support the compounds of this invention as acting as highly selective agonistic ligands for integrin $\alpha_v\beta_3$ on osteocyte and chondrocyte lineage cells.

Fifth, the natural binding partners of integrins that promote biological functions (e.g., bone resorption, cancer metastasis, inflammation, etc.) via integrins are large molecules in most cases. See Table 1. Small molecule binding partners for integrins are only known as their inhibitors. The examples of the compounds of this invention are small, chemically synthesized peptides. This invention frontiers new possibilities of identifying small molecules that are agonistic molecules to integrins.

Lastly, this invention is useful in identifying a more advanced therapeutic drug that can treat osteoarthritis, and possibly treat other joint or hard tissue disorders. For example, an orally available compound could be designed based on the specific information from this invention.

Earlier studies with the peptide of SEQ ID No: 10 and its orthologues indicated that sustained exposure of hard tissue cells to these compounds or continuous infusion of these compounds in vivo did not add a merit as compared to periodic administrations. Namely, a long half-life is not needed for the group of compounds of this invention. This may be advantageous in identifying an orally available compound.

Compounds of this Invention

This invention discloses a group of compounds that regulate 3D bone shape change and have unique binding properties to osteocyte cell surface integrins.

These compounds are useful therapeutics to treat joint and hard tissue diseases and disorders, including but not limited to osteoarthritis, rheumatoid arthritis, joint trauma, osteoporosis, disc herniation, spinal injury, or temporomandibular disorder.

The compounds selectively bind integrin $\alpha_v\beta_3$ on osteocytes with a binding affinity that is at least 300 times higher than the affinities to other integrins: $\alpha_v\beta_1$, $\alpha_v\beta_6$, $\alpha_v\beta_8$, $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_9\beta_1$, or $\alpha_{10}\beta_1$.

Their binding affinity to integrin $\alpha_v\beta_3$ is even further (>300 times) higher than the affinities to the integrins: $\alpha_7\beta_1$, $\alpha_8\beta_1$, $\alpha_L\beta_2$, $\alpha_M\beta_2$, $\alpha_X\beta_2$, $\alpha_D\beta_2$, $\alpha_{IIb}\beta_3$, $\alpha_6\beta_4$, $\alpha_E\beta_7$, $\alpha_4\beta_7$, or $\alpha_{11}\beta_1$.

The only other integrin that the compounds bind is integrin $\alpha_v\beta_5$; however, their binding affinities to this integrin are at least three times lower than those to the integrin $\alpha_v\beta_3$.

The selective binding of the compounds to integrin $\alpha_v\beta_3$ on osteocytes is agonistic, promoting a biological cascade that leads to slowing or arresting of age-associated or pathological 3D shape change of the bones, in particular, subchondral bones in the joints.

The compounds can be peptides comprising 20-50 amino acids containing a general amino acid sequence of SEQ ID No: 1: DLXXRGDNDXXPFSGDGXXF, where X is any amino acid.

A cyclic peptide having SEQ ID No: 1 is within the scope of this invention.

Peptides with other amino acid sequence than the amino acid sequence of SEQ ID No: 1 that is an agonist to integrin $\alpha_v\beta_3$, an agonistic monoclonal antibody to integrin $\alpha_v\beta_3$, and a non-peptide agonist to integrin $\alpha_v\beta_3$ are also within the scope of this invention, insofar as they fulfill the unique integrin binding property and biological activities described in this invention. Irrespective of the type of a compound, a compound with these properties can be identified using integrin binding assay and biological experiments described in detail below. Any known agonists to integrin $\alpha_v\beta_3$ that fulfill the unique integrin binding property and biological activities described in this invention are within the scope of this invention as well.

A pharmaceutical composition comprising a pharmaceutically acceptable carrier and a pharmaceutically effective amount of any one of these compounds is a part of this invention.

Evaluation of Biological Effects

Once a compound having the unique integrin binding properties of this invention is identified, its biological effects can be assessed with in vitro and/or in vivo studies.

An example of in vitro study is measuring TGF-β signaling in the cultured osteocyte by measuring phosphorylation of Smad3, which is an effector phosphorylated and activated by active TGF-β receptor complex. The culture media should contain a suboptimal level of TGF-β. If the compound of interest works, type I and type II TGF-β receptors should be assembled, bind TGF-β in the media, form an active TGF-β receptor complex, and upregulate Smad3 phosphorylation. Alternative to the Smad3 phosphorylation measurement, upregulation of expression of matrix metalloproteinase-13 (MMP-13) can be measured by transcription or protein production levels.

If using an in vivo assay, the compound of interest is administered to a mouse by intra-articular injection or subcutaneous injection near a joint and the length and/or number of canaliculi of the osteocytes can be assessed in the subchondral bone of the treated joint (Mazur, 2019).

The relevance of these assays with the anticipated biological effects is explained in the following section.

Overall Mechanisms of Osteocyte Homeostasis and 3D Bone Shape Maintenance

The effect of the compounds of this invention on maintenance of osteocyte homeostasis and 3D bone shape are via selective activation of TGF-β signaling in osteocytes in the subchondral bones in a joint.

Binding of the compounds of this invention to integrin $\alpha_v\beta_3$ on the osteocytes triggers cytoskeletal change in the cells. The cytoskeletal change then induces assembly of TGF-β receptor types I and II, which are separately located on the cell membrane, to form a complex of TGF-β receptor I and II. This TGF-β receptor complex becomes susceptible to a binding with endogenous TGF-β.

The TGF-β receptor complex bound by its ligand (i.e., endogenous TGF-β) is then phosphorylated and activated ("active TGF-β receptor complex"). The active TGF-β receptor complex is known to trigger phosphorylation and activation of its effector Smad3. The activated Smad3 is known to translocate to nucleus of the cell, then binds with Runx2 transcription factor and triggers the transcription of the essential molecules for cell homeostasis such as MMP-2, MMP-13, MMP-14, Cathepsin K, carbonic anhydrase 2. Adequate expression and functioning of these molecules prevent excessive bone mineralization and sclerosis.

The TGF-β signaling is critical to maintain the number and length of canaliculi of the osteocytes. The sufficient number and length of canaliculi connects osteocytes to form a cell-cell network, believed to be critical to maintaining 3D bone shape. Healthy canaliculi formation and expression of the homeostatic enzymes listed above are correlated and believed to be regulated together.

As described in the Background, normal canaliculi formation is critical to maintaining alignment of collagen matrix in the bone, and healthy 3D bone shape. Canaliculi formation is also mediated by TGF-β signaling via binding of the compounds of this invention to the integrin $\alpha_v\beta_3$ on osteocytes.

Clinical Effects of the Compounds and Pharmaceutical Composition

The compounds and pharmaceutical compositions comprising thereof described in this invention slow, arrest, or reverse 3D bone shape change, particularly in the subchondral bones.

As demonstrated in the natural history studies from the OAI database, 3D bone shape change precedes articular cartilage degeneration in osteoarthritis (OA). A main feature of 3D shape change of the subchondral bones is flattening of the plateaus and edges of the articulating bones (e.g., in the case of a knee, the femoral condyle and tibial plateau). The flattened bones expand in area and ultimately can form osteophytes. Osteophytes physically damage not only the overlying articular cartilage but also the cartilage of the articulating bone, and, in the case of a knee, the menisci. The osteophytes also press into surrounding soft tissues and synovial membranes, causing significant pain and inflammation (synovitis).

3D bone shape change, including osteophyte formation, is often associated with excessive mineralization and/or sclerosis of the bone. The compounds of this invention reduce the excessive bone mineralization and/or sclerosis as a part of its slowing effect of pathological 3D bone shape change.

Method of Impacting Bone Structure

The present invention also presents a method of impacting bone structure.

One aspect of the method of this invention is method of delaying, arresting, or reversing 3D bone shape change, which is either pathological or as a consequence of natural aging.

The method is particularly useful in treating joint diseases and disorders.

The method can be used in treatment of one or more of osteoarthritis, rheumatoid arthritis, joint trauma, osteoporosis, disc herniation, spinal injury, or temporomandibular disorder, particularly when these conditions affect one or more of the joints of knee, hip, ankle, hand, finger, wrist, elbow, shoulder, spine, or jaw.

The method comprises measuring 3D bone shape change in a joint, administering a pharmaceutical composition comprising a pharmaceutically acceptable carrier and a pharmaceutically effective amount of one of the compounds of this invention, and measuring the 3D bone shape change again.

The effects of this treatment method can be monitored by comparing the 3D bone shapes in the first and second measurements and/or by monitoring clinical signs and symptoms.

3D bone shape in a joint can be typically measured by conventional magnetic resonance imaging (MRI).

The obtained images are typically analyzed by a mathematical algorithm based on active appearance models (AAMs) (Williams 2010).

The extent of the 3D bone shape change can be determined by z-score where average healthy 3D bone shape is specified as score of zero (0).

An example of this scoring is the B-score (Bowes 2019).

As far as the obtained image can be analyzed by such algorithm, the image can be obtained by other imaging methodologies including but not limited to radiography, computer tomography (CT), or ultrasound, provided, however, that the first and the second image acquisitions need to be conducted using the same methodology and imaging protocol.

Administration of the pharmaceutical composition can be chosen from intra-articular, topical, subcutaneous, intra-cutaneous, intra-dermal, intravenous, or oral, depending on the bioavailability and pharmacodynamics of the active ingredient in the composition.

For example, the peptides of SEQ ID No: 1-14 can be administered by intra-articular injection or subcutaneous injection near the target joint bone. The clinical study of the peptide of SEQ ID No: 10 demonstrated that intra-articular injection is highly effective. See EXAMPLE 2 below.

In case of small joints such as those in the fingers, subcutaneous, intra-cutaneous, or intra-dermal injections to the adjacent area of the joint to be treated should be useful. Micro-needles for these administrations are available equipment for these administrations.

Whether intra-articular or other types of injections, these peptides can be administered once, twice, three times, four times, or more.

The interval of the administrations can be chosen from every 1-10 days, every other week, every three weeks, every month, every 2-24 months, and so forth.

One series of treatment can consist of 1-6 injections.

The frequency and interval of administration can be determined by comparing the first and second measurements of 3D shape of the joint bone of interest.

Treatment of Bone Fracture

Another aspect of the method of impacting bone structure is accelerating bone fracture healing by administration to a patient the pharmaceutical composition of this invention.

The bone fractures can be caused by any one or more of osteoporosis, osteoarthritis, rheumatoid arthritis, trauma, spinal injury, and/or disc herniation.

The healing process of the bone fracture can be monitored using conventional imaging tools including but not limited to magnetic resonance (MR), radiography (X-ray), computer tomography (CT) and ultrasound.

With any of these imaging tools, the method comprises; obtaining a first image of the bone fracture prior to administering the pharmaceutical composition; obtaining a second image of the bone fracture after administration of the pharmaceutical composition; comparing the first and second images; determining the therapeutic impact of the pharmaceutical composition on the bone fracture healing; and determining a need for additional administration based on the comparison.

Cartilage Formation and Repair

Besides bone cells, integrin $\alpha_v\beta_3$ is known to be expressed by chondroblasts or chondroprogenitor cells as one of the integrins expressed by them.

The compounds of this invention may bind integrin $\alpha_v\beta_3$ on chondroprogenitor cells or chondroblasts, thereby promote cartilage formation or repair, in addition to their activities on osteocyte homeostasis and 3D bone shape maintenance.

For chondroblasts or chondroprogenitor cells, the mechanism that the compounds promote cartilage formation is different from that in the maintenance of osteocyte homeostasis and 3D bone shape.

In response to binding of one of the compounds of this invention to integrin $\alpha_v\beta_3$ on chondrocyte or chondroprogenitor cells, cytoskeletal changes, assembly of active TGF-β receptor complex, and phosphorylation and activation of the effector Smad3 (and possibly Smad2) occur in a similar manner to the those in the osteocytes.

However, when the activated Smad3 is translocated to the nucleus, it binds with a transcription factor Sox9. The formed transcription factor complex triggers transcriptions of the molecules needed for cartilage formation; type II collagen and aggrecan.

The biological activities of the compounds in this subgroup on chondrocytes or chondroprogenitor cells can be assessed by measuring expression of type II collagen and/or aggrecan by the cells (Middleton-Hardie 2010) or Smad3 phosphorylation in the cells.

Integrin $\alpha_v\beta_3$ is also known to be expressed by synoviocytes (synovial cells), which are derived from mesenchymal stem cells (Morshed 2019). A subgroup of the compounds of this invention can also selectively bind integrin $\alpha_v\beta_3$ of synoviocytes and induce their migration to cartilage, where they can differentiate into chondrocytes. This also contributes articular cartilage formation and repair.

A subgroup of the compounds of this invention selectively binds integrin $\alpha_v\beta_3$ on chondroprogenitor cells or chondroblasts in addition to integrin $\alpha_v\beta_3$ on osteocytes. These compounds can delay pathological 3D bone shape change and promote articular cartilage repair in a joint simultaneously. It is a synergistic advantage when such compounds are used to treat OA and other joint diseases and disorders.

The pharmaceutical composition comprising a therapeutically effective amount of any compound in this subgroup and a pharmaceutically acceptable carrier is within the scope of this invention.

Clinical use of this pharmaceutical composition provides a method to treat OA and other joint diseases and disorders by acting on both delaying 3D shape change of subchondral bone and cartilage repair or formation.

Articular cartilage thickness and/or volume can be measured by conventional MRI. The same MRI image can be used to measure both cartilage thickness and 3D joint bone shape.

Therefore, the method comprises; measuring cartilage thickness and 3D shape of subchondral bone of the affected joint; administering the pharmaceutical composition comprising a therapeutically effective amount of the compound of this subgroup; and a pharmaceutically acceptable carrier; measuring cartilage thickness and 3D shape of subchondral bone of the joint again after the administration.

The comparison of the first and the second measurements shows the efficacy of the treatment on the subchondral bone and cartilage.

Treatment of Joint Pain and/or Function Impairment

The compound and pharmaceutical composition of this invention were proven to improve joint pain, function, and other clinical conditions in addition to the structural improvements of bone and cartilage. Such clinical benefits by the compound and pharmaceutical composition of this invention appear even more robust in more advanced conditions. See EXAMPLE 2.

These broad and robust clinical benefits by the compound and pharmaceutical composition of this invention are believed primarily to be the results of the structural improvements of bone and cartilage.

Since the compound of this invention preferably binds specific integrins expressed by bone and cartilage lineage cells, it is also believed that their cellular metabolisms are modified, that their release of nociceptor agonists and/or pro-inflammatory molecules are decreased, and/or that their release of analgesic and/or anti-inflammatory molecules may be increased.

The method to treat patients suffering from pain, function impairment, and/or other clinical symptoms of a joint that were improved in the clinical study described in the EXAMPLE 2 using the compounds or pharmaceutical compositions of this invention is within the scope of this invention.

The method comprises identifying a patient suffering from pain, function impairment and/or other clinical conditions of a joint and administering such patient a compound or a pharmaceutical composition of this invention.

The pain, function impairment, and other joint conditions can be those associated with one or more of osteoarthritis, rheumatoid arthritis, trauma, osteoporosis, spinal injury, disc herniation, or temporomandibular disorder affecting any joint of knee, hip, ankle, finger, hand, wrist, elbow, shoulder, spine, or jaw.

The pain, function impairment, and other joint conditions can be those associated with natural aging.

The joint pain treated by the method or the use of the compound or pharmaceutical composition of this invention can be the one associated with or without any joint activity. Pain frequency can be reduced as well.

The function impairment of a joint treated by the method or the use of the compound or pharmaceutical composition of this invention can be the one involving any joint activity, including, but not limited to, bending, straightening, twisting, or rotating of the joint.

Administration of the compounds or pharmaceutical composition of this invention can be by subcutaneous injection, intra-articular injection, or oral administration.

The treatment effects on the joint pain, function, or other clinical parameters can be measured by patient reported outcome measures or casual question and answer between a caregiver and a patient.

The patient reported outcome measures for the treatment effects can be chosen based on the target joint and measurement.

For instance, if the target is a knee joint and the pain and/or function impairment is associated with osteoarthritis, Western Ontario and McMaster University Osteoarthritis Index (WOMAC) or Knee injury and Osteoarthritis Outcome Score (KOOS) can be used. If knee pain and/or function impairment is for a knee injury, KOOS can be used. If the target is a hip joint and the conditions are associated with osteoarthritis or an injury, Hip disability and Osteoarthritis Outcome Score (HOOS) can be used. A numerical rating scale (NRS) or visual analogue scale (VAS) are broadly used to assess pain intensity in any joint.

The treatment effect can be measured by;
1) measuring or identifying joint pain and/or function impairment prior to administering the compound or the pharmaceutical composition of this invention;
2) measuring or identifying joint pain and/or function impairment after administration of the compound or the pharmaceutical composition;
3) comparing the results from the first and the second measurements or identifications; and
4) determining the therapeutic effect of the compound or the pharmaceutical composition on the joint pain and/or function.

EXAMPLES

The following examples are put forth so as to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Competition ELISA of Integrins Bound by Different Peptides

Objective and Outline of the Study

In order to test whether the compounds known to slow 3D bone shape change and form articular cartilage have any binding affinity to any integrin expressed by hard tissue cells, a preliminary binding study was conducted.

The integrins known to be expressed by one or more of hard tissue cells were used for the study as the candidate "disease modifying integrins" binding to which modifies 3D bone shape change and cartilage formation in osteoarthritis.

Initially, the following 14 integrins were chosen for initial screening for binding to the peptide of SEQ ID No: 10: $\alpha_v\beta_1$, $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_8\beta_1$, $\alpha_9\beta_1$, and $\alpha_{10}\beta_1$. Since the peptide of SEQ ID No: 10 contains an RGD integrin binding region, integrins known to bind RGD were tested.

In addition to integrins known to bind RGD, several other integrins known to bind other sequences (e.g., collagen binding integrins) were also tested to look for non-specific integrin binding to the peptide of SEQ ID No: 10. There are 24 known integrins, and the 14 that were tested were chosen to include RGD binding integrins and a representative sample of other non-RGD binding integrins.

Following the initial screening experiments, the following integrins were chosen for further evaluation based on showing any detectable signal above background or putative role in bone or cartilage biology: $\alpha_v\beta_1$, $\alpha_v\beta_3$, $\alpha_v\beta_5$, $\alpha_v\beta_6$, $\alpha_v\beta_8$, $\alpha_1\beta_1$, and $\alpha_2\beta_1$. These integrins were tested for binding using the competition ELISA method outlined below.

For the integrin-binding molecule side, the peptides of SEQ ID No: 10 and 12, as well as a scramble peptide of the peptide of SEQ ID No: 15 were used.

```
                                            (SEQ ID No: 10)
TDLQERGDNDISPFSGDGQPFKD (SEQ ID No: 12)
PDLQERGDNDISPFSGDGQPFKD (SEQ ID No: 15)
GFQDSLDSNRQDPGTDPEKGIDF
```

Materials and Methods

Methods were carried out as follows, as described by Bernhagen 2017.

Reagents and Chemicals.

Incubation and washing buffers were prepared using standard protocols. Recombinant human integrins were purchased from R&D Systems (Minneapolis, U.S.A.). Strep-HRP (Streptavidin-Horseradish Peroxidase conjugate, Southern-Biotech, Birmingham, U.S.A.), and rabbit anti-mouse-HRP (Southern-Biotech, Birmingham, U.S.A.) were diluted 1:200-1:1000 for ELISA experiments.

Amino acids were purchased from Iris Biotech (Marktredwitz, Germany) and Matrix Innovation (Quebec, Canada). Resins were purchased from Rapp Polymere (Tübingen, Germany) and Merck (Darmstadt, Germany). $MnCl_2 \cdot 4H_2O$ was purchased from Sigma-Aldrich (Steinheim, Germany). $CaCl_2 \cdot 2H_2O$ and $MgCl_2 \cdot 6H_2O$ were purchased from Merck (Darmstadt, Germany). Tween80 was purchased from Faryon (Capelle, The Netherlands) and I-Block was purchased from Tropix (Bedford, U.S.A.).

All peptides were synthesized via Fmoc-based solid-phase peptide synthesis (SPPS) on a Rink-amide resin using standard protocols. All peptides were purified by preparative HPLC on an RP-C18 column (Reprosil-Pur 120 C18-AQ 150×20 mm, Dr. Maisch GmbH, Ammerbuch, Germany) using an $ACN/H_2O$ gradient (5-65%), including 0.05% TFA, followed by lyophilization.

Competition ELISA.

All integrins were dissolved according to manufacturer's protocol and stored in 25 µL aliquots of 100 µg/mL in PBS. For coating of one 96 well plate, 2 aliquots were thawed and dissolved in 9.95 mL of cold coating buffer for a 0.5 µg/mL solution.

After coating, the plates were subsequently sealed and stored at 4° C. overnight.

Integrin was removed and plates were blocked with 150 µL 1% I-Block solution for 1 h at room temperature.

The following washing and incubation steps were performed according to manuscript. ABTS substrate buffer was prepared by mixing substrate buffer pH 4, 20 g/L ABTS and 3% $H_2O_2$ in the volumetric ratio 10/0.25/0.02. Peptides, whose integrin binding strength were to be determined, were mixed in 12 different concentrations (each 3-fold dilutions) with a fixed concentration of RGD-Knottin (both in PBS, 15 min, room temperature), followed by incubation of the plates with peptide/RGD-Knottin solutions.

Substrate buffer incubation and absorbance measurements were identical to that for binding ELISA. All experiments were carried out in triplicate. $IC_{50}$ values were calculated via nonlinear regression analysis using GraphPad Prism software and represent the peptide concentration at which 50% inhibition of biotinylated knottin binding is observed.

Results and Discussions

As shown in FIG. 1, binding of the peptide of SEQ ID No: 10 was highly selective for the $\alpha_v\beta_3$ integrin.

Figure 2:
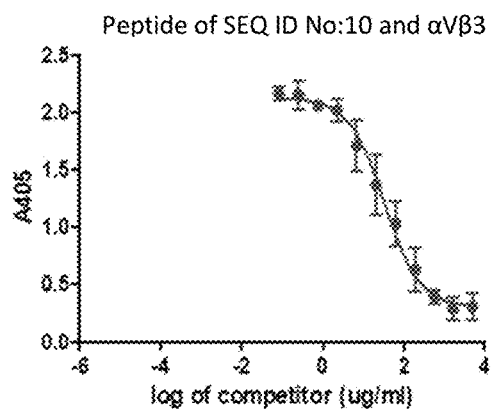
FIG. 2 is a graph demonstrating binding affinity of the peptide of SEQ ID No: 10 and integrin $\alpha_v\beta_3$. The peptide exhibited a binding affinity of approximately 33 µg/mL.

Using the methods described above, the IC50 was determined to be approximately 30 μg/mL (FIG. 2).

Figure 3:
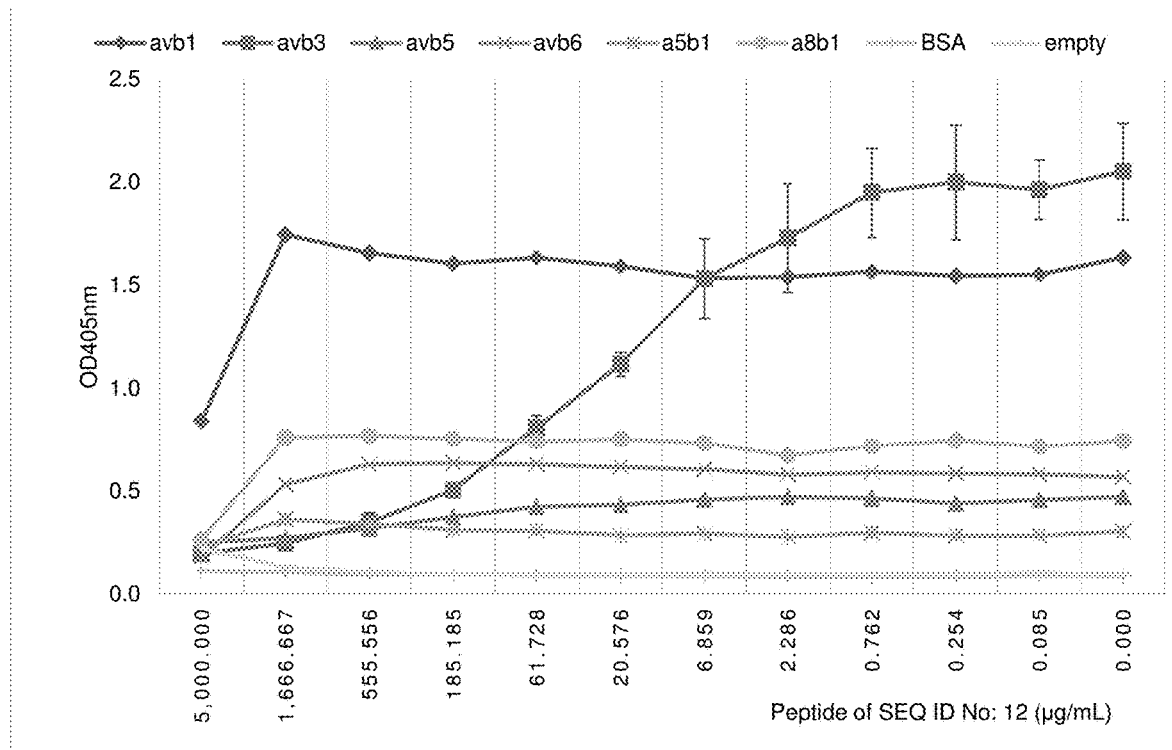
FIG. 3 is a graph exhibiting the results of competitive ELISA with Knottin Peptide comparing the binding of various integrins to the peptide of SEQ ID No: 12. The peptide demonstrated more potent binding to integrin $\alpha_v\beta_3$ than all other integrins.
Figure 4:
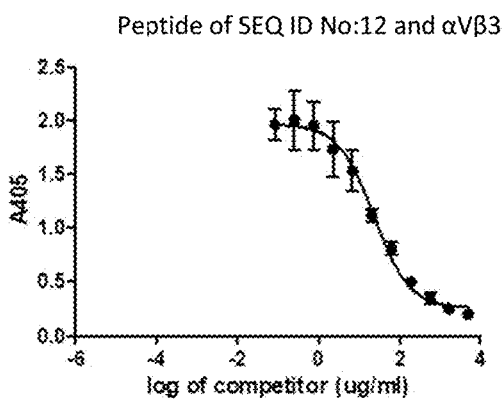
FIG. 4 is a graph showing binding affinity of the peptide of SEQ ID No: 12 and integrin $\alpha_v\beta_3$. The peptide demonstrated a binding affinity of approximately 23 µg/mL.

The peptide of SEQ ID No: 12 was also tested. The binding affinity of this peptide to integrin $\alpha_v\beta_3$ was similar to that of the peptide of SEQ ID No: 10 and was also highly selective for the $\alpha_v\beta_3$ integrin (FIGS. 3 and 4).

In order to confirm that the binding was due to the RGD integrin binding motif, the peptide of SEQ ID No: 10 was randomly scrambled (SEQ ID No: 15) and tested for its ability to bind integrins.

Figure 5:
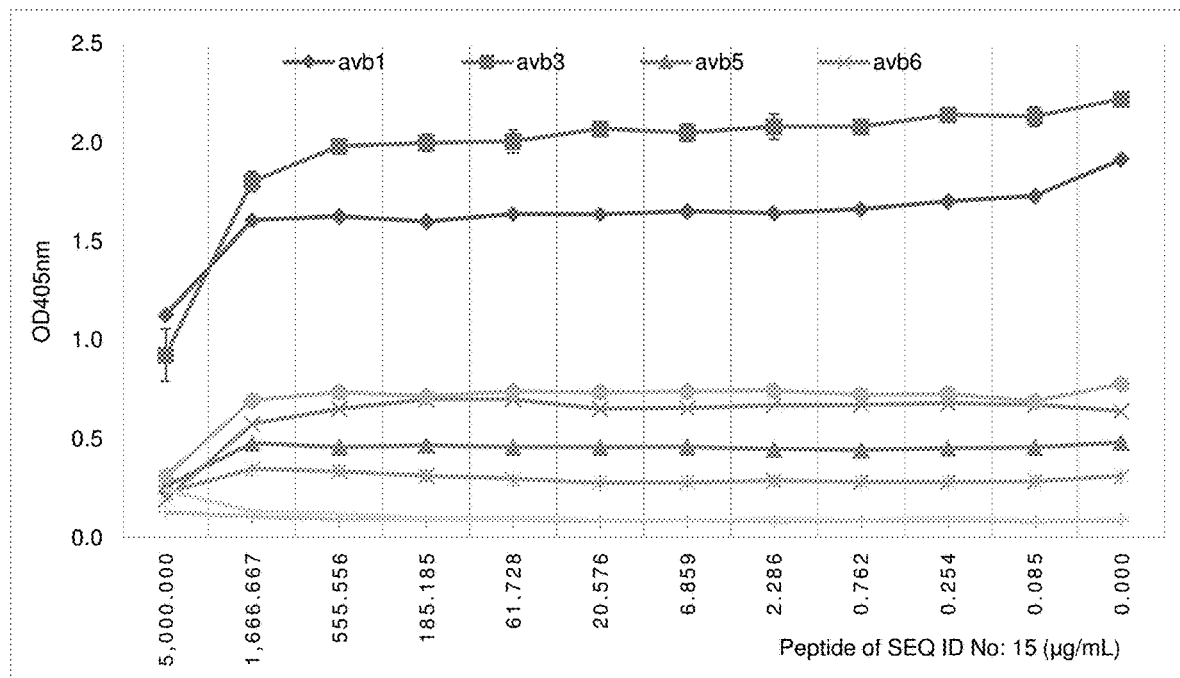
FIG. 5 is a graph demonstrating the results of competitive ELISA with Knottin Peptide comparing the binding of various integrins to the peptide of SEQ ID No: 15. The peptide did not bind any of the integrins.
Figure 6:
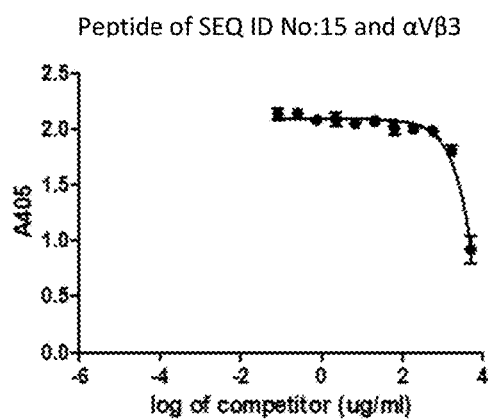
FIG. 6 is a graph exhibiting binding affinity of the peptide of SEQ ID No: 15 and integrin $\alpha_v\beta_3$. The peptide showed no binding affinity within the limits of the binding assay (<1,000 µg/mL). It is likely over 10,000 µg/mL, or could be above 100,000 µg/mL.

As shown in FIG. 5, there was no significant binding to any integrin tested.

The peptide of SEQ ID No: 10 was derived from a central portion of the human matrix extracellular phosphoglycoprotein (MEPE) molecule (Hayashibara 2004). This region of MEPE contain an RGD sequence which is known to be an important integrin binding motif, however, previously, it was not known which integrin that MEPE or its fragment peptide binds to. These experiments confirm a selective binding to the $\alpha_v\beta_3$ integrin.

A weaker binding to integrin $\alpha_v\beta_5$ was also observed.

Example 2

Clinical and Structural Efficacies of a Peptide that Binds to Integrins on Bone and Cartilage Cells Clinical Study Methodology
Outline of the Study A peptide of SEQ ID No: 10 that showed selective binding to integrins $\alpha_v\beta_3$ and a weaker binding to $\alpha_v\beta_5$ was tested for its clinical safety as well as clinical and structural efficacies in mild to severe knee OA patients.

A multicenter, randomized double-blind, placebo-controlled study was designed to investigate the safety, tolerability, pharmacokinetics, and efficacy of the peptide of SEQ ID No: 10 administered in four weekly doses in subjects with bilateral knee osteoarthritis. The study was conducted under an open IND (investigational new drug application) at CDER (Center for Drug Evaluation and Research) of the U.S. FDA (The United States Food and Drug Administration) in compliance with GCP (Good Clinical Practice) and ICH (International Conference on Harmonization of Technical Requirements for Registration of Pharmaceuticals for Human Use) guidelines. Eighteen (18) orthopedic, rheumatologic, and family practice centers in the U.S. participated in the study.

The study was divided into Part A and Part B. The Part A was designed to evaluate safety of intra-articular (I.A.) administration of the peptide of SEQ ID NO: 10 (TPX-100) at different dosing levels (20, 50, 100, or 200 mg per injection in sequential cohorts) in the subjects with osteoarthritis of the knees and to select a dose for Part B. Part B was to evaluate safety and efficacy of the selected dose of the peptide of SEQ ID No: 10.

The 200 mg dose was selected for Part B. Data from 93 subjects was qualified for drug efficacy analysis of clinical benefits (pain, function, etc.), each of whom received 4 once-weekly injections of 200 mg/dose of the peptide of SEQ ID No: 10 in the Index knee and identical placebo in the contralateral knee (Control knee), as randomly assigned. No other doses of drug or placebo were administered. All subjects visited their respective clinical sites at 3, 6, and 12 months after the first dosing for their safety and efficacy assessments.

MRI of both knees were obtained from these 93 subjects at baseline, 6 and/or 12 months. They were sent to the central readers of cartilage thickness and 3D bone shape, respectively. Both central readers were blinded to the treatment assignment and clinical data throughout their analysis process.

For the 3D bone shape analyses, its central reader first made a qualification review of all MRI images from the 93 subjects since they were obtained primarily for cartilage thickness measurement. The images from 15 subjects were removed from the analysis as they did not provide sufficient quality for 3D bone shape analysis.

MRIs from the remaining 78 subjects (156 knees: 78 Index and 78 Control) were qualified for analysis of 3D shape of the knee joint bones (B-scores of femur, tibia, and patella).

Screening of the Subjects

After informed consent was obtained, subjects underwent a clinical and laboratory screening evaluation at which their preliminary eligibility for the study was evaluated. Screening included the following procedures:
  Medical history including medication history
  Focused physical examination
  Vital signs including resting blood pressure, pulse, respiratory rate, and temperature
  Weight, height, and BMI
  X-ray of the knees (if not obtained within 3 months of screening)
  Laboratory evaluations including hematology, coagulation profile, comprehensive metabolic panel, etc.
  Recording of concomitant medications Subjects who met all clinical and laboratory eligibility criteria underwent standardized bilateral knee MRIs.

Inclusion and Exclusion Criteria

Inclusion and exclusion criteria for screening of the subjects for either Part A or Part B were as follows:
  Inclusion Criteria
  1. Age≥25 and ≤75
  2. Patello-femoral osteoarthritis of both knees of mild to moderate severity with intact meniscus and ligamentous stability (cruciate and collateral ligaments)
     Clinically, as determined by screening questionnaire, judgment of the Principal Investigator (may be supporting by imaging studies of knees); confirmed by centrally read screening MRI of both knees, of ICRS Grade 1-3, or Grade 4 with only focal defects, no defect greater than 1 cm.
     Meniscus intact (MRI degenerative signal up to and including grade II acceptable)
     Cruciate and collateral ligament stability as defined by clinical examination
  3. Able to read, understand, sign and date the subject informed consent 4. Willingness to use only acetaminophen as the primary analgesic (pain-relieving) study medication. The maximum dose of acetaminophen must not exceed 4 grams/day (4000 mg) per day.
5. Willingness to use only hydrocodone/acetaminophen or hydrocodone alone for breakthrough pain during the injection period (through study day 30).
6. Willingness not to use non-steroidal anti-inflammatory drugs (NSAIDS) such as aspirin, ibuprofen or naproxen for the first 30 days of the study.
7. Female subjects of childbearing potential who are sexually active (non-abstinent) must agree to and comply with using 2 highly effective methods of birth control (oral contraceptive, implant, injectable or indwelling intrauterine device, condom with spermicide, or sexual abstinence) while participating in the study.

Exclusion Criteria

1. Contraindication to MRI, including: metallic fragments, clips or devices in the brain, eye, or spinal canal; implanted devices that are magnetically programmed; weight >300 lbs.; moderate or severe claustrophobia; previous intolerance of MRI procedure
2. ICRS greater than Grade 3, excepting Grade 4 with focal defects no greater than 1 cm as confirmed by centrally-read screening MRI
3. MRI evidence of inflammatory or hypertrophic synovitis, or significant chondral calcification
4. Prior surgery in the knees, excluding procedures for debridement only
5. Knee joint replacement or any other knee surgery planned in the next 12 months
6. History of rheumatoid arthritis, psoriatic arthritis, or any other autoimmune or infectious cause for arthritis
7. Knee effusion >2+ on the following clinical scale:
Zero=No wave produced on downstroke
Trace=Small wave on medial side with downstroke
1+=Larger bulge on medial side with downstroke
2+=Effusion spontaneously returns to medial side after upstroke (no downstroke necessary)
3+=So much fluid that it is not possible to move the effusion out of the medial aspect of the knee
8. Last viscosupplementation (e.g., Synvisc® or similar hyaluronic acid product) injected into either knee <3 months before screening
9. Last intra-articular knee injection of corticosteroids <2 months before screening
10. Use of any steroids (except inhaled corticosteroids for respiratory problems) during the previous month before screening
11. Known hypersensitivity to the peptide of SEQ ID No: 10
12. Known hypersensitivity to acetaminophen or hydrocodone
13. History of arthroscopy in either knee in the last 3 months before screening
14. History of septic arthritis, gout or pseudo-gout, of either knee in previous year before screening
15. Clinical signs of acute meniscal tear (e.g., locking or new acute mechanical symptoms consistent with meniscal tear)
16. Patellar chondrocalcinosis on X-Ray
17. Skin problem, rash or hypersensitivity, affecting either knee at the injection site
18. Bleeding problem, platelet or coagulation deficiency contraindicating intra-articular injection
19. Active systemic infection
20. Current treatment or treatment within the previous 2 years prior to the Screening Visit for any malignancy except basal cell or squamous cell carcinoma of the skin, unless specific written permission is provided by the Sponsor's medical monitor
21. Women of childbearing potential who are pregnant, nursing, or planning to become pregnant, and those who do not agree to remain on an acceptable method of birth control throughout the entire study period
22. Participation in other clinical osteoarthritis drug studies, with the exception of analgesic studies, within one year prior to screening
23. Currently taking Paclitaxel (mitotic inhibitor), and or Natalizumab (anti-integrin).
24. History of significant liver disease or consumption of more than 3 alcoholic drinks a day. (Definition of one alcoholic drink: 12-ounces of beer, 8-ounces of malt liquor, 5-ounces of wine, 1.5-ounces or a "shot" of 80-proof distilled spirits or liquor such as gin, rum, vodka, or whiskey).

Randomizaton

If all clinical inclusion and exclusion criteria were met, MRIs of both knees were obtained and evaluated by a central reader to determine the ICRS grade (gICRS) of each knee as the final screening criterion. If the cartilage of patello-femoral compartment in both knees fell within ICRS grades 1-3, or 4 with only small focal defects no greater than 1 cm, the subject was registered. The randomization center randomized each subject to either "Right knee active" or "Left knee active". The active knee was to receive the peptide of SEQ ID No: 10 and the contralateral knee was to receive identical placebo.

For enrolled subjects, there was within-subject randomization, such that one knee received active drug injections, and the contralateral knee received identical placebo injections. As two knees within a person form a matched set, the effects of individual-level confounders (e.g., level of activity, genetic and epigenetic factors, pain threshold) are eliminated, increasing the power of the study to detect a treatment effect if one is present.

Any subject who was randomized in Part A was excluded from enrollment in Part B.

Dosing

On the first dosing day, the randomized subjects were assessed by physical examinations and vital signs. Further, they completed the Knee injury and Osteoarthritis Outcome Score (KOOS), which includes the Western Ontario and McMaster Universities Osteoarthritis Index (WOMAC). The KOOS questionnaire assesses knee-specific activities of daily living, sports and recreation, knee-related quality of life, other symptoms such as stiffness, and knee pain. The KOOS has been used extensively in longitudinal studies of knee osteoarthritis. After assessments were completed, subjects received one intra-articular injection in each knee, with each injection prepared from the vial(s) marked for that knee. One knee received the peptide of SEQ ID No: 10, and the contralateral knee received placebo with subject, site, and sponsor blinded to treatment assignment. Subjects were monitored for adverse events during the injections and for a few hours after the injections. Vital signs were also monitored after the injections.

On the 7th, 14th, and 21st days after the first dosing, subjects received the second, third, and fourth (last) dosing of the same study materials, respectively. Safety and adverse event assessments were obtained as on the first dosing day.

Post-Treatment Follow-Up

Subjects returned to their respective study sites at 3, 6 and 12 months after the first dosing day for follow-up evaluations. In addition, the study sites monitored the subject's condition through telephone contact 9 months after the first dosing day. During the 3, 6, and 12 months post-treatment, subjects were evaluated on site with physical examinations, vital signs, serum chemistries, as well as completing patient-reported outcomes including the KOOS. Adverse events and concomitant medications were recorded. MRIs of both knees were obtained during the 6 and 12-month visits.

Efficacy Analyses

All KOOS subscale scores, WOMAC Total score and subscale scores, MRI-based patello-femoral and tibiofemoral cartilage thickness, and MRI-based subchondral bone area and 3D bone shape were analyzed.

MRI images were provided to central readers for cartilage and subchondral bone measures, respectively. Central readers were blind as to treatment assignment.

3D shape of subchondral bone was analyzed using active appearance model (AAM) software developed by Imorphics (www.imorphics.com) specifically for assessing these parameters in the osteoarthritic knee.

Statistical analyses were carried out using a two-sided t-test at the 5% level of significance. The outcome variables were the differences of the change of the score of each subscale of KOOS and WOMAC, change of cartilage thickness, subchondral bone area, and 3D bone shape score ("B-score") change from baseline to 6 and 12 months in the treated knee ("Index Knee") compared with the placebo-exposed knee ("Control Knee").

Results

Structural and Clinical Efficacies in OA Knees of All Severity

In the analysis of all 93 subjects, Index knee treated with 200 mg per dose of the peptide of SEQ ID No: 10 demonstrated clinically meaningful and statistically significant (as compared to Control knee treated with identical placebo) improvements in several WOMAC and KOOS subscales and questions at 6 months, 12 months, or both time points (McGuire 2017 and McGuire 2018).

On the other hand, cartilage thickness change in neither patello-femoral nor tibiofemoral compartment showed significant difference between Index and Control knees throughout the 12-month follow-up period.

Of the 93 subjects, MRI of 78 (156 knees) had sufficient quality to provide reliable 3D bone shape (B-score) data. These subjects were re-analyzed for their knee structure and clinical parameters.

Approximately 34% of all 156 knees had gICRS 4 (the most severe) knee cartilage defects, all of which were in the tibiofemoral (TF) compartment. Another approximately 45% had gICRS 3 (the second most severe) knee cartilage defects in patello-femoral (PF) and/or TF compartments, and the remaining approximately 21% had gICRS 2 (moderate) PF and/or TF in one or both knees. There were no subjects with gICRS 1 (mild) knee OA. Distribution of the severity by gICRS was very similar between Index and Control knees. The mean body mass index (BMI) of all subjects exceeded 30, which is in the obese range and consistent with the average BMI for the OA population in the U.S. The average age of the subjects was 58.4 and 62% of the subjects were female. These were also consistent with the demographic of the U.S. OA population. Most subjects had severe OA in one or both knees.

Treatments with peptide of SEQ ID No: 10 were safe and well tolerated. There were no severe adverse events that were related to the peptide of SEQ ID No: 10. Treatment-related adverse events were mild or moderate, transient, and common in many subjects at baseline.

Figure 7:
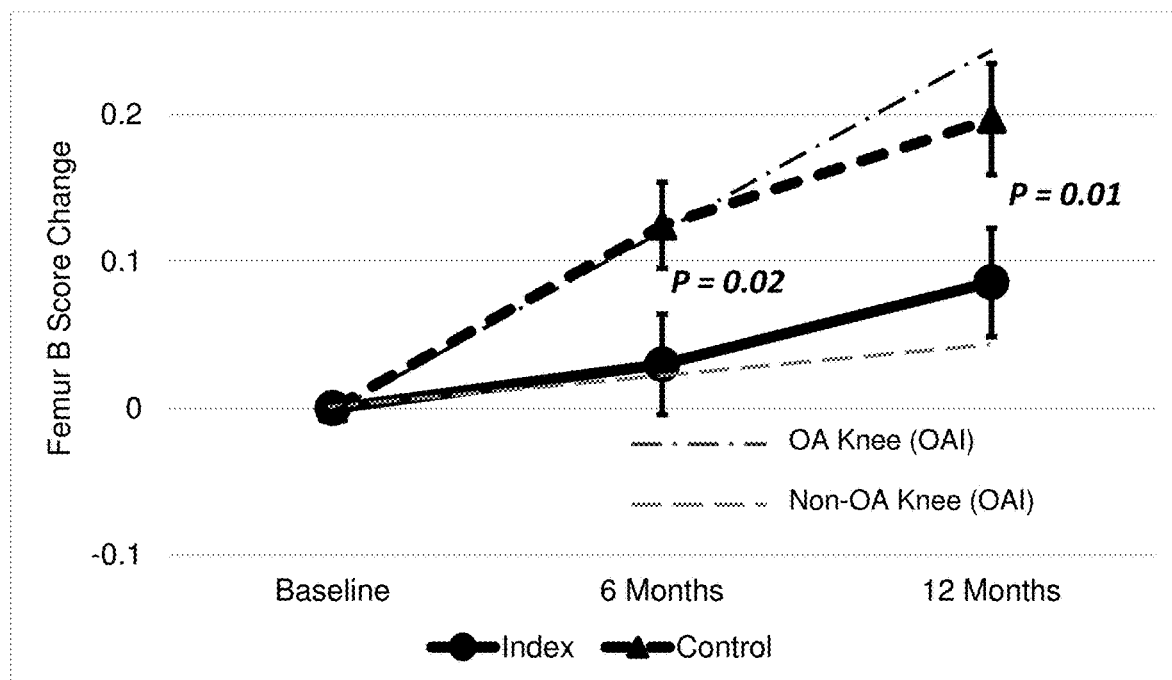
FIG. 7 is a graph showing a result of a clinical study indicating pathological 3D bone shape change in femur in moderate to severe knee OA patients. Seventy-eight (78) Index and Control knees, respectively, were treated with the peptide of SEQ ID No: 10 or identical placebo administered by intra-articular (IA) injections on days 0, 7, 14, and 21. The graph shows the mean femur B-score changes from baseline and the error bars indicate the standard error of the mean. Paired Student's t-test indicated significant reductions of pathological B-score changes in Index knee as compared to Control knee at 6 and 12 months with p values of 0.02 and 0.01, respectively. The trajectory of the B-score change in Control knee was similar to that of the OA knees in the OAI (Osteoarthritis Initiative) database. The trajectory of the B-score change in Index knee was similar to that of the non-OA knees in the OAI database.

Three-dimensional (3D) subchondral bone shape change of femur as quantified by B-score showed a statistically significant (p<0.05) difference in favor of Index Knee as compared to Control Knee at both 6 and 12 months. See FIG. 7. The trajectory of the B-score change in Control knee was similar to that of the OA knees in the OAI (Osteoarthritis Initiative) database. The trajectory of the B-score change in Index knee was similar to that of the non-OA knees in the OAI database.

Three-dimensional (3D) subchondral bone shape changes in tibia and patella also demonstrated slower increases in Index Knee as compared to Control Knee.

Patient-reported outcomes (PROs) including WOMAC and KOOS subscales demonstrated clinically meaningful and statistically significant improvements in the Index knees (treated with peptide of SEQ ID No: 10) as compared to the Control knees (treated with identical placebo).

Figure 8:
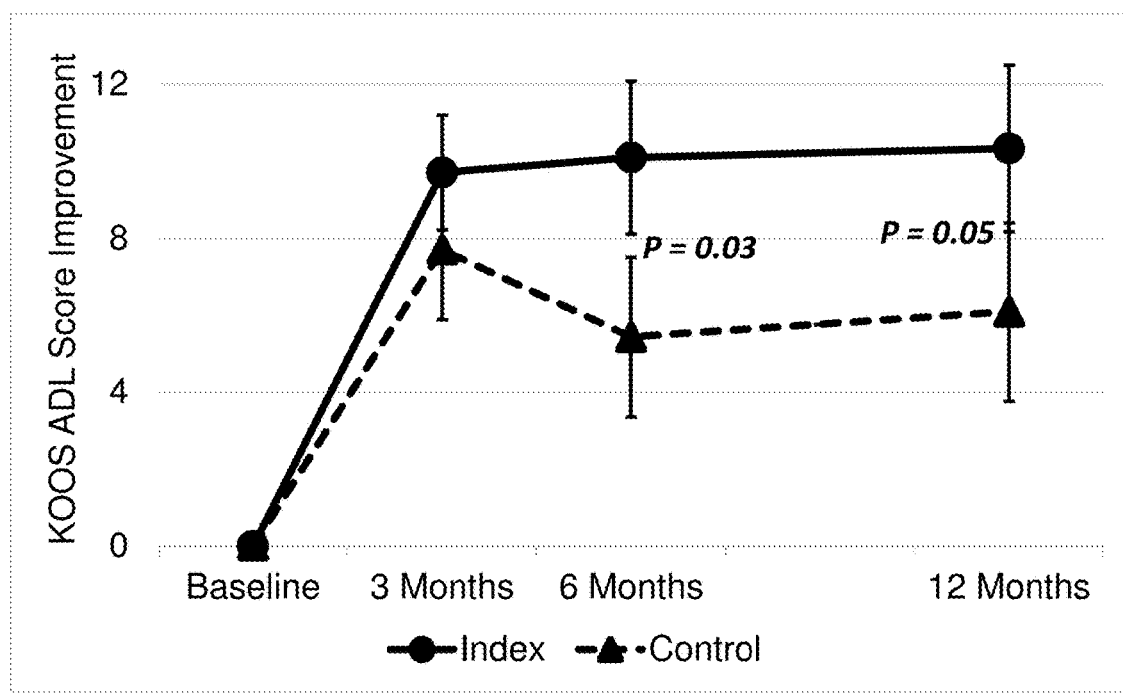
FIG. 8 is a graph showing a result of a clinical study demonstrating knee function improvement measured by KOOS ADL (Activities of Daily Living) in moderate to severe knee OA patients. Seventy-eight (78) Index and Control knees, respectively, were treated with the peptide of SEQ ID No: 10 or identical placebo administered by IA injections on days 0, 7, 14, and 21. The graph shows the mean KOOS ADL score improvements from baseline and the error bars represent the standard error of the mean. Paired Student's t-test showed superior knee function improvement in Index knee as compared to Control knee at 6 and 12 months with p values of 0.03 and 0.05, respectively.

The KOOS ADL (Function in Activities of Daily Living) subscale consists of 17 questions pertaining to various daily activities critical to everyday knee function. Results of the KOOS ADL domain demonstrated clinically meaningful and statistically significant (p<0.05) improvements over baseline in Index knee as compared to Control knee at both 6 and 12-month time points. See FIG. 8. The WOMAC Function subscale, which consists of the same questions as KOOS ADL, unsurprisingly also showed the same robust improvement in Index knee as compared to Control knee.

The KOOS Knee-related Quality of Life (QOL) subscale consists of four questions including the subjects' general difficulty with their knee and awareness of problems with confidence regarding each of their knees. The KOOS Knee-related QOL exhibited clinically meaningful and statistically significant improvement in Index knee as compared to Control knee at 12 months.

The KOOS Pain subscale and WOMAC Pain domain, respectively, demonstrated a clinically meaningful improvement in Index knee at 12 months, although the difference with Control knees did not reach statistical significance.

Figure 9:
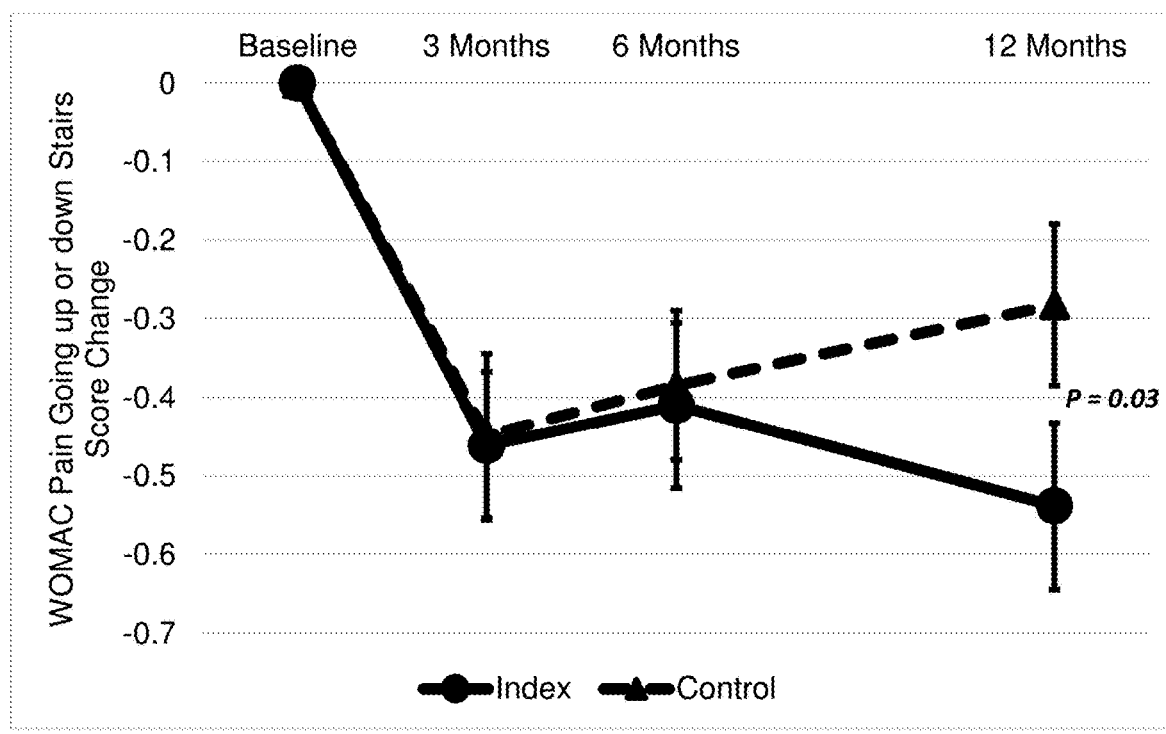
FIG. 9 is a graph demonstrating a result of a clinical study demonstrating improvement of KOOS Pain going up or down stairs in moderate to severe knee OA patients. Seventy-eight (78) Index and Control knees, respectively, were treated with the peptide of SEQ ID No: 10 or identical placebo administered by IA injections on days 0, 7, 14, and 21. The graph shows the mean pain intensity score changes from baseline (negative change is better) and the error bars indicate the standard error of the mean. Paired Student's t-test indicated superior improvements of pain intensity in Index knee as compared to Control knee at 12 months with p values of 0.03.

One of the questions making up the KOOS Pain (and WOMAC Pain) subscale queries "Pain going up or down stairs". Pain during this common activity is one of the most common complaints made by patients with knee OA and was significantly improved (p<0.05) in Index knee as compared to Control knee at 12 months. See FIG. 9.

Figure 10:
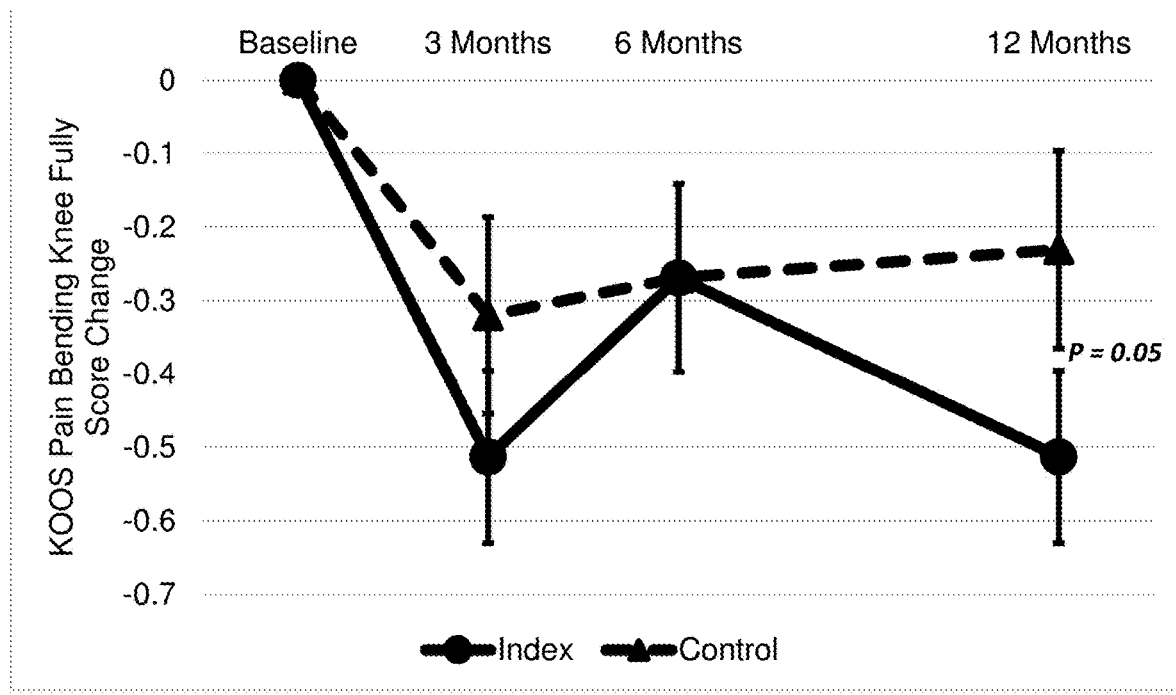
FIG. 10 is a graph exhibiting a result of a clinical study showing improvement of KOOS Pain bending knee fully in moderate to severe knee OA patients. Seventy-eight (78) Index and Control knees, respectively, were treated with the peptide of SEQ ID No: 10 or identical placebo administered by IA injections on days 0, 7, 14, and 21. The graph shows the mean pain intensity score changes from baseline (negative change is better) and the error bars indicate the standard error of the mean. Paired Student's t-test indicated superior improvements of pain intensity in Index knee as compared to Control knee at 12 months with p values of 0.05.

Another question making up the KOOS Pain (but not WOMAC Pain) subscale queries "Pain bending knee fully" was also significantly improved (p<0.05) in Index knee as compared to Control knee at 12 months. See FIG. 10. "Bending knee fully" is one of the most stringent knee activities applying a large burden to the knee joint and it is required in multiple functions.

It should be noted that Index knee showed statistically significant improvements as compared to Control knee in multiple domains making up KOOS ADL and WOMAC Function subscale queries, including "Descending Stairs," "Ascending Stairs," "Bending to floor/pickup an object," "Getting in and out of Car," "Getting in and out of bath," "Getting on/off Toilet," etc. These activities particularly require more bending and force on the knees than others.

Figure 11A:
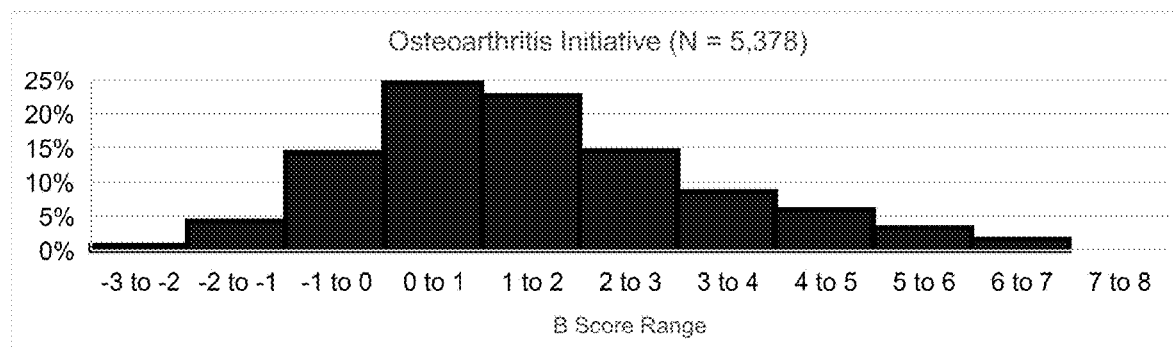
FIGS. 11a, 11b, and 11c are histograms comparing distributions of baseline femur B-score of 5,378 OA knees in the OAI database (11a), 78 OA knees assigned to the treatment with the peptide of SEQ ID No: 10 (11b), and 78 OA knees assigned to the treatment with placebo (11c) in the clinical study. The distributions were very similar among the three groups of knees. The mean femur B-scores of the groups were nearly identical, which were 1.52, 1.48, and 1.48, respectively.
Figure 11B:
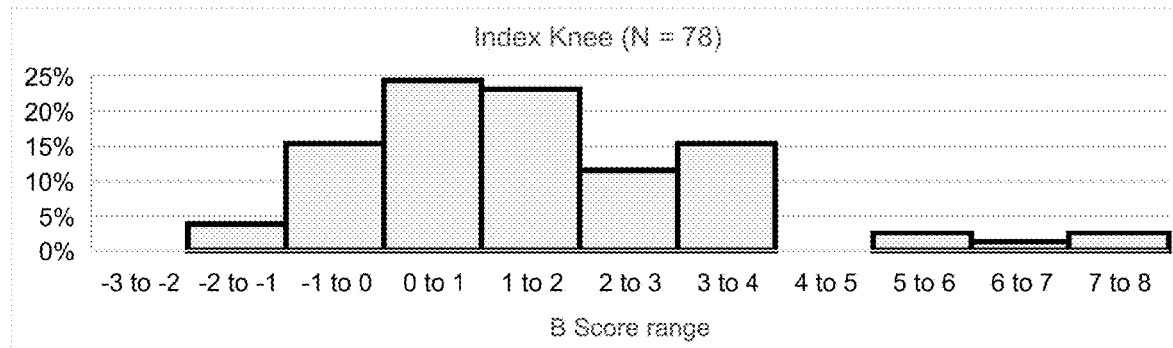
Figure 11C:
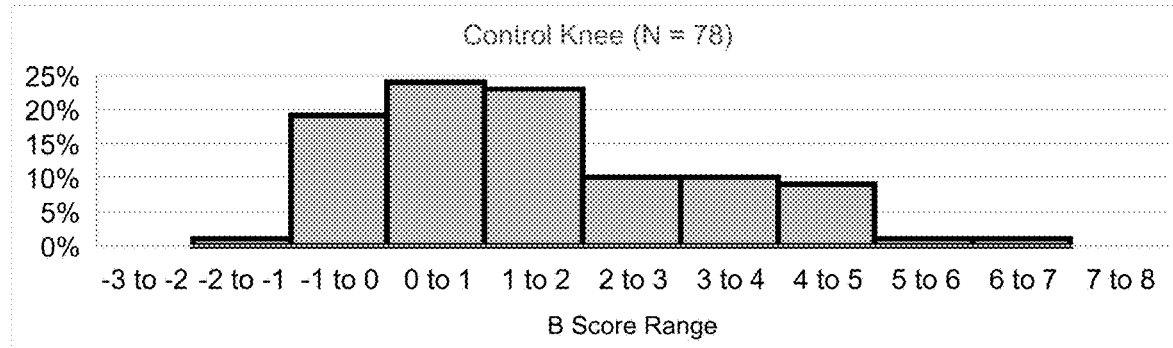

Distribution of B-scores of the 78 Index Knees and 78 Control Knees, respectively, at the baseline was very similar to that of over 5,000 OA knees registered in the National Institutes of Health-Osteoarthritis Initiative (NIH-OAI) database. The means of the baseline B-scores of Index and Control knees were the same each other (1.48), and very similar to that of the OA knees in the NIH-OAI database (1.52). These mean that the subjects (knees) enrolled in this study well represented the severity distribution of knee OA in the U.S. See FIGS. 11a, 11b and 11c.

These structural and clinical data in moderate to severe knee OA patients demonstrate that the peptide of SEQ ID No: 10, which selectively binds to integrin $\alpha_v\beta_3$ expressed by osteocytes reduces pathological 3D shape changes of subchondral bone in multiple knee compartments and provides critical benefits to patients including improvements in knee function and pain.

Since it has been known that the peptide of SEQ ID No: 10 (a human orthologue) and its least homologous peptide of SEQ ID No: 14 (a rat/murine orthologue) interchangeably show biological activities in the bone cells of the other species, it is reasonable to assume that a peptide sharing a consensus amino acid sequence of SEQ ID No: 1 has the same clinical and structural efficacy in a joint, in particular, in a knee joint.

Structural and Clinical Efficacies in the Knees with More Advanced OA

As shown in FIG. 11, distributions and mean values of B-scores of the 78 Index Knees and 78 Control Knees, respectively, at the baseline were very similar to that of over 5,000 OA knees in the NIH-OAI database.

In natural history studies of knee OA using the NIH-OAI database, it has been demonstrated that femur B-score reliably predicts knee pain and function impairment. The higher the femur B-score is, the more probable the knee suffers from pain and function impairment.

We analyzed structural and clinical efficacies of the peptide of SEQ ID No: 10 as compared to placebo in the knees with higher baseline B-scores, i.e., knees with more advanced OA defined by 3D bone shape.

The placebo-exposed (Control) knee with higher femur Baseline B-Score, i.e., more advanced knee OA, showed faster increase in their femur B-scores during the 12-month study period. For instance, Control knee with the femur Baseline B-Score ≥0.5 increased the B-score faster than those with the femur Baseline B-Score ≥0. Likewise, the 12-month femur B-score increase was faster in Baseline B-Score ≥21 cohort than ≥0.5 cohort, and Baseline B-Score ≥1.5 cohort than ≥1.0 cohort. It was consistent with the observation in the natural history study with the OAI database, which showed more rapid femur B-score increase in more advanced (higher B-score) OA knees.

Figure 12:
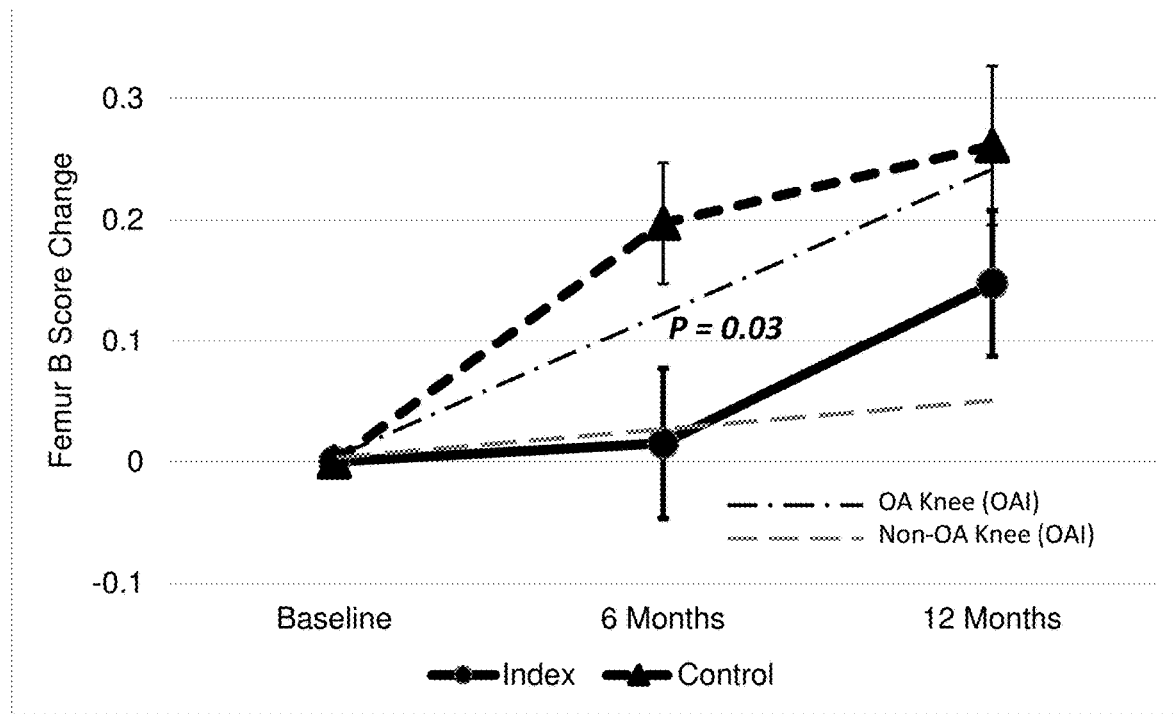
FIG. 12 is a graph showing a result of a clinical study exhibiting pathological 3D bone shape change in femur in a more severe knee OA cohort. From the seventy-eight (78) Index and Control knees, respectively, the knees with baseline B-score ≥1.5 were compared for their 12-month B-score changes. The numbers of the knees in Index and Control groups were 35, respectively. Index and Control knees were treated with the peptide of SEQ ID No: 10 or identical placebo, respectively, administered by IA injections on days 0, 7, 14, and 21. The graph shows the mean femur B-score changes from baseline and the error bars indicate the standard error of the mean. Since Index and Control knees do not necessarily belong to the same subjects, unpaired Student's t-test was employed for the statistical analysis. The test indicated significant reductions of pathological B-score changes in Index knee as compared to Control knee at 6 months with p value of 0.03. The trajectory of the B-score change in Control knee was steeper than that of the OA knees in the OAI (Osteoarthritis Initiative) database. The trajectory of the B-score change in Index knee was similar to that of the non-OA knees in the OAI database particularly for the first 6 months after the treatment.

FIG. 12 shows 12-month B-score changes of the knees with Baseline B-Score ≥1.5, which had more advanced knee OA than the average at the baseline as shown in FIG. 11. The trajectory of the B-score change in Control knee was steeper than that of all OA knees in the OAI database.

On the other hand, the trajectory of B-score change in Index knee was very similar to that of non-OA (healthy) knees in the OAI database particularly for the first 6 months after the treatment. The trajectory was increased in the second 6 months as compared to the first 6 months but femur B-score of Index knee at 12 months were maintained markedly lower than that of Control knee. See FIG. 12.

Figure 13:
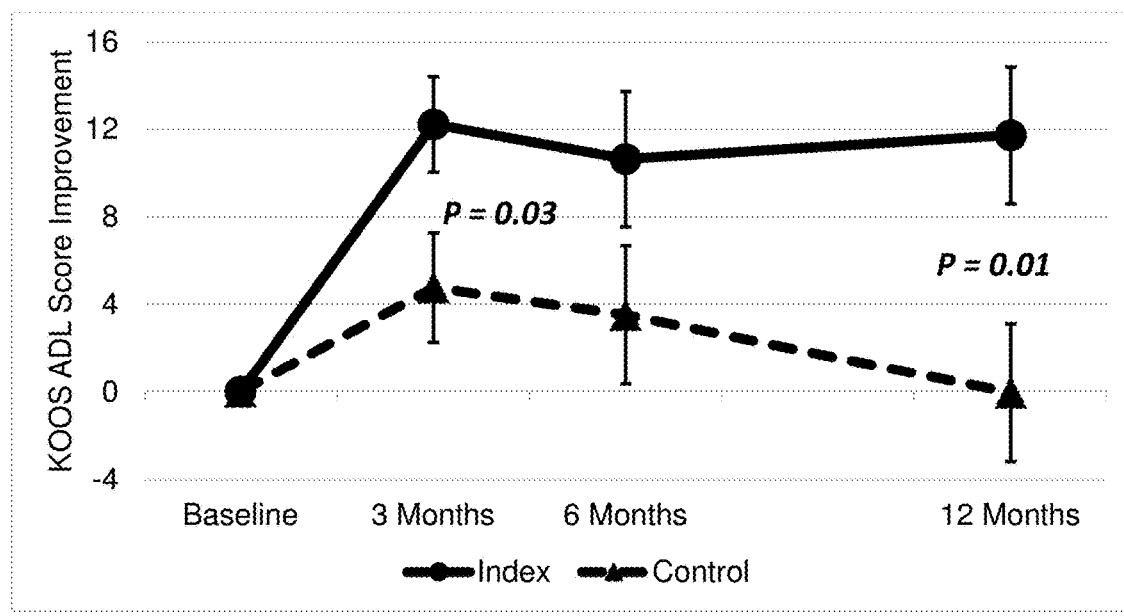
FIG. 13 is a graph showing a result of a clinical study demonstrating knee function improvement measured by KOOS ADL (Activities of Daily Living) in the more severe knee OA cohort, which is the same as those in FIG. 12. Unpaired Student's t-test showed statistically significant knee function improvement in Index knee as compared to Control knee at 3 and 12 months with p values of 0.03 and 0.01, respectively.

Knee function measured by KOOS ADL, which is the same as WOMAC Function, in Index knee of this cohort showed clinically meaningful improvement at 3 months after treatment, which was maintained through 6 and 12 months without additional treatment. Control knee showed minor and non-meaningful function improvement at 3 months but was declined to zero by 12 months. See FIG. 13.

Figure 14:
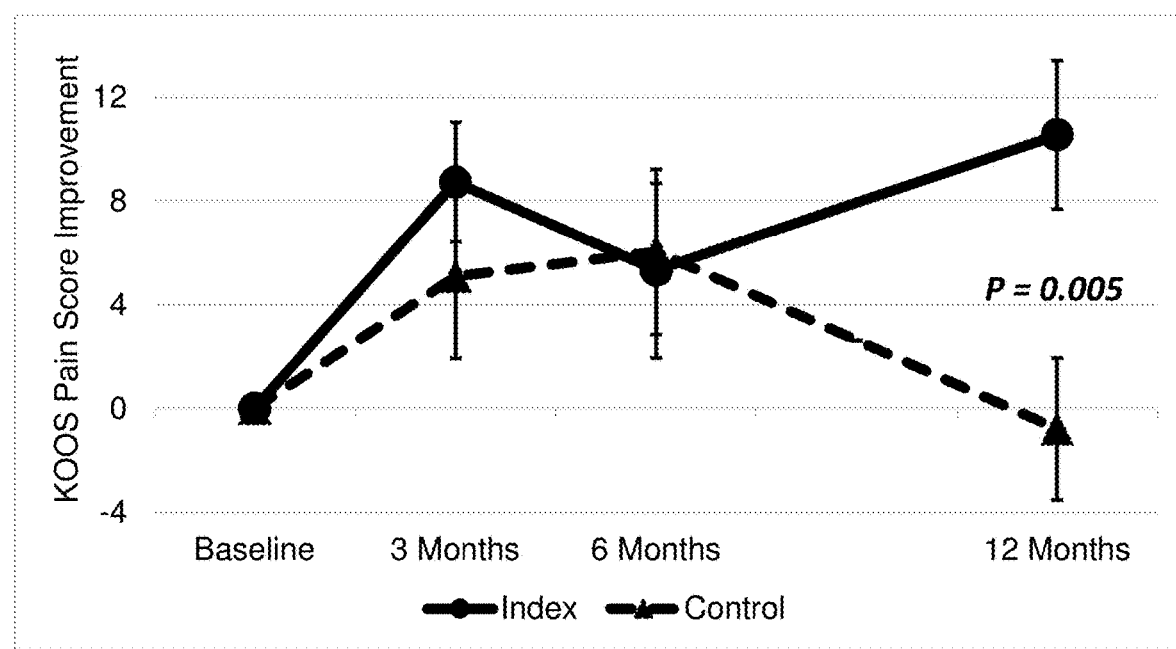
FIG. 14 is a graph showing a result of a clinical study demonstrating knee pain improvement measured by KOOS Pain in the more severe knee OA cohort, which is the same as those in FIGS. 12 and 13. Unpaired Student's t-test showed statistically significant knee pain improvement in Index knee as compared to Control knee at 12 months with p value of 0.005.

Similarly, knee pain measured by pain subscales of WOMAC and KOOS, respectively, showed more robust improvement in Index knee as compared to Control knee in a higher femur Baseline B-Score cohort. Initial minor improvement in Control knee, which is believed to be a placebo effect, was also declined to zero by 12 months. See FIG. 14.

A notable difference from function improvement was that statistically significant pain improvement in Index knee as compared to Control knee occurred at 12 months. Most patients participated in this study had had knee OA for years. It is common that those with chronic pain are sensitized in their pain center in the central nervous system, and that the pain center is consistently activated with or without nociceptive pain signals. In such patients, it requires an extra time to "desensitize" the pain center after the pathogen of the pain (i.e., pathological bone shape change in the knee joint in the case of knee OA) has been treated. This is believed to be the reason for the delayed improvement in pain as compared to the improvements of 3D bone shape and function.

These clinical study data indicate that treatment of OA patients with a compound selectively binds to integrin $\alpha_v\beta_3$ on bone and cartilage cells results in clinically meaningful patient's benefits including improvements in joint pain and function. Such clinical efficacies appear even more robust in more advanced disease.

REFERENCES

Alday-Parejo B, Stupp R, Ruegg C. Are integrins still practical targets for anti-cancer therapy? *Cancers.* 2019; 11,978

American Academy of Orthopaedic Surgeons. Projected volume of primary and revision total joint replacement in the U.S. 2030 to 2016. Research News released on Mar. 6, 2018.

American Academy of Orthopaedic Surgeons. Treatment of Osteoarthritis of the Knee—2nd Edition Evidence-Based Clinical Practice Guideline. Published May 18, 2013

Barczyk M, Carracedo S, Gullberg D. Integrins. *Cell Tiss Res.* 2010; 339:269-280

Barr A, Dube B, Hensor E, Kingsbury S, Peat G, Bowes M, Sharples L, Conaghan P. The relationship between three-dimensional knee MRI bone shape and total knee replacement—a case control study: data from the Osteoarthritis Initiative. *Rheumatology.* 2016; 55: 1585-1593

Bernghagen D, De Laporte L, Timmerman P. High-affinity RGD-knottin peptide as a new tool for rapid evaluation of the binding strength of unlabeled RGD-peptides to integrin receptors. *Anal Chem* 2017; 89:5991-5997

Biemacka A, Dobaczewski M, Frangogiannis N. TGF-β signaling in fibrosis. *Growth Factors.* 2011. October; 29(5):196-201

Bingham C, Buckland-Wright C, Garnero P, Cohen S, Dougados M, Adami S, Clauw D, Spector T, Pelletier J, Raynauld J, Strand V, Simon L, Meyer J, Cline G, Beary J. Risedronate decreases biochemical markers of cartilage degeneration but does not decrease symptoms or slow radiographic progression in patients with medial compartment osteoarthritis of the knee. *Arthritis & Rheumatism.* 2006:54(11); 3494-3507

Borst A, James Z, Zagotta W, Ginsberg M, Rey F, DiMaio F, Backovic M, Veesler D. The herapeutic antibody LM609 selectively inhibits ligand binding to human $\alpha_v\beta3$ integrin via steric hinderance. *Structure.* 2017 Nov. 7; 25(11)1732-1739

Bowes M, Vincent G, Wolstenholme C, Conaghan P. A novel method for bone area measurement provides new insights into osteoarthritis and its progression. *Ann Rheum Dis.* 2013; 74:519-525

Bowes M, Kacena K, Alaba O, Brett A, Bodick N, Conaghan P. Machine learning defines the relationship between structural knee osteoarthritis and Patient-Important Outcomes: An 8-year study of 47,858 knee MRIs from the Osteoarthritis Initiative (OAI). *ACR Abs.* 2019; Abs 2196

Bowes M, Kacena K, Alabas O A, Brett A D, Dube B, Bodick N, Conaghan P G. Machine-learning, MRI bone shape and important clinical outcomes in osteoarthritis: data from the Osteoarthritis Initiative. *Ann Rheum Dis.* 2020; 0:1-7. doi:10.1136/annrheumdis-2020-217160

Cheng S, Lai C, Blystone S, Avioli L. Bone mineralization and osteoblast differentiation are negatively modulated by integrin $\alpha_v\beta3$. *J of Bone and Min Res.* 2001; 16(2):277-288

Cohen M D. Hyaluronic acid treatment (viscosupplementation) for OA of the knee. *Bull Rheum Dis.* 1998; 47:4-7

Cooke M E, Allon A A, Cheng T, Kuo A C, Km H T, Vail T P, Marcucio R S, Schneider R A, Lotz J C, Allison T. Structured three-dimensional co-culture of mesenchymal stem cells with chondrocytes promotes chondrogenic differentiation without hypertrophy. *Arthritis and Cartilage.* 2011; 19:1210-1218

Dube B, Bowes M, Barr A, Hensor E, Kingsbury S, Conaghan P. The relationship between two different measures of osteoarthritis bone pathology, bone marrow lesions and 3D bone shape: data from the osteoarthritis initiative. *Osteo and Cart.* 2018; 26:1333-1337

Engleman V, Nickols G, Ross F, Horton M, Griggs D, Settle S, Ruminski P, Teitelbaum S. L. A peptidomimetic antagonist of the $\alpha v\beta3$ integrin inhibits bone resorption In vitro and prevents osteoporosis In vivo. *J Clin Invest.* 1997; 99(9):2284-2292

Erggelet C, Vavken P. Microfacture for the treatment of cartilage defects in the knee joint—A golden standard. *J of Clin Ortho and Trauma.* 2016; 7:145-152

FDA (U.S. Department of Health and Human Services, Food and Drug Administration). Osteoarthritis: Structural endpoints for the development of drugs, devices, and biological products for treatment Guidance for Industry. *DRAFT GUIDANCE* August 2018

Fraioli R, Rechmacher F, Neubauer S, Manero J, Gil J, Kessler H, Mas-Moruno C. Mimicking bone extracellular matrix: Integrin-binding peptidomimetic enhance osteoblast-like cells adhesion, proliferation, and differentiation on titanium. *Colloids and Surfaces B: Biointerfaces.* 2015; 128:191-200

Gramoun A, Shorey S, Bashutski J, Dixon J, Sims S, Heersche J, Manolson M. Effects of Vitaxin, a novel therapeutic in trial for metastatic bone tumors, on osteoclast functions In vitro. *J of Cell Biochem.* 2007:102; 341-352

Guermazi A, Kalsi G, Niu J, Crema M, Copeland R, Orlando A, Noh M, Roemer F. Structural effects of intra-articular TGF-β1 in moderate to advanced knee osteoarthritis: MRI-based assessment in a randomized controlled trial. *BMC Musculoskeletal Disord.* 2017; 18:461

Haj-Mirzaian A, Guermazi A, Roemer F W, Bowes M A, Conaghan P G, Demehri S. Bisphosphonates intake and its association with changes of periarticular bone area and three-dimensional shape: data from the osteoarthritis Initiative (OAI). *Osteo and Cart.* 2018; 26:564-568

Hayashibara T, Hiraga T, Yi B, Nomizu M, Kumagai Y, Nishimura R, Yoneda T. A synthetic peptide fragment of human MEPE stimulates new bone formation in vitro and in vivo. *JBMR.* 2004; 19:455

Hellio le Graverand M, Clemmer R, Redifer P, Brunell R, Hayes C, Brandt K, Abramson S, Manning P, Miller C, Vignon E. A 2-year randomized, double-blind, placebo-controlled, multicenter study of oral selective iNOS inhibitor, cindunistat (SD-6010), in patients with symptomatic osteoarthritis of the knee. *Ann Rheum Dis.* 2013; 72:187-195

Hochberg M C, Guermazi A, Guehring H, Aydemir A, Wax S, Fleuranceau-Morel P, Bihlet A R, Byrjalsen I, Andersen J, Eckstein F. Efficacy and safety of intra-articular Sprifermin in symptomatic radiographic knee osteoarthritis: results of the 2-year primary analysis from a 5-year randomized, placebo-controlled, Phase 2 study. *Arthr Rheum.* 2017; 69(10):1L Hochberg M, Guermazi A, Guehring H, Aydemir A, Wax S, Fleuranceau-Morel P, Bihlet A, Byrjalsen I, Andersen J, Eckstein F. Efficacy and safety of intra-articular Sprifermin in symptomatic radiographic knee osteoarthritis: pre-specified analysis of 3-year data from a 5-year randomized, placebo-controlled, Phase II study. *Osteo and Cart.* 2018; 26:S32

Horton M. Integrin antagonist as inhibitors of bone resorption: implications for treatment. *Proceedings of the Nutrition Soc.* 2001; 60:275-281

Huang R, Rofstad E. Integrins as therapeutic targets in the organ-specific metastasis of human malignant melanoma. *J of Exp & Clin Cancer Res.* 2018; 37:92

Hunter D, Nevitt M, Lynch J, Kraus V, Katz J, Collins J, Bowes M, Guermazi A, Roemer F, Losina E. Longitudinal validation of periarticular bone area and 3D shape as biomarkers for knee OA progression?Data from the FNIH OA Biomarkers Consortium. *Ann Rheum Dis.* 2016; 75:1607-1614

Karsdal M, Byrjalsen I, Alexandersen P, Bihlet A, Andersen J, Riis B, Bay-Jensen A, Christiansen C. Treatment of symptomatic knee osteoarthritis with oral salmon calcitonin: results from two phase 3 trials. *Osteoarthritis Cartilage.* 2015; 23(4):532

Kok R, Schraa A, Bos E J, Moorlag H E, Asgeirsdottir S A, Everts M, Meijer D K F, Molema G. Preparation and functional evaluation of RGD-modified proteins as $\alpha v\beta3$ integrin directed therapeutics. *Bioconjugate Chem.* 2002: 13; 128-135

Krzeski P, Buckland-Wright C, Balint G, Cline G A, Stoner K, Lyon R, Beary J, Aronstein W S, Spector T D. Development of musculoskeletal toxicity without clear benefit after administration of PG-116800, a matrix metalloproteinase inhibitor, to patients with knee osteoarthritis: a randomized, 12-month, double-blind, placebo-controlled study. *Arthr Res Ther.* 2007; 9(5):R109

Laslett L L, Dore D A, Quinn S J, Boon P, Ryan E, Winzenberg T M, Jones G. Zolendronic acid reduces knee pain and bone marrow lesions over 1 year: a randomized controlled trial. *Ann Rheum Dis.* 2012; 71:1322-8

Lazarov M, Shih M S, Gerome C, Blacher R, Kumagai Y, Rosen D M. AC-100, a fragment of MEPE, promotes fracture healing in a rat model. *ASBMR* 2004.

Lee B, Parvizi J, Bramlet D, Romness D, Guermazi A, Noh M, Sodhi N, Khlopas A, Mont M. Results of a phase II study to determine the efficacy and safety of genetically engineered allogeneic human chondrocytes expressing TGF-β1. *J Knee Surgery.* 2020; 33:1n67-172

Liu Z, Wang F, Chen X. Integrin $\alpha v\beta3$-targeted cancer therapy. *Drug Dev Res.* 2008; 69(6):329-339

Loeser R. Integrins and chondrocytes-matrix interactions in articular cartilage. *Matrix Biol.* 2014 October; 39:11-16

Marie P. Targeting integrins to promote bone formation and repair. *Nature* 2013; 9; 288-295

Marie P, Teti A. Integrins and other cell surface attachment molecules of bone cells. *Principles of Bone Bio.* 2020; 17; 401-422

Mazur C, Woo J, Yee C, Fields A, Acevado C, Bailey K, Kaya S, Fowler T, Lotz J, Dang A, Kuo A, Vail T, Alliston T. Osteocyte disfunction promotes osteoarthritis through MMP13-dependant suppression of subchondral bone homeostatis. *Bone Res.* 2019; 7:34

McAlindon T, LaValley M, Harvey W, Price L, Driban J, Zhang M, Ward R. Effect of Intra-articular triamcinolone vs saline on knee cartilage volume and pain in patients with knee osteoarthritis—a randomized clinical trial. *JAMA.* 2017; 317(19):1967-1975

McGuire D, Lane N, Segal N, Metyas S, Barthel H R, Miller M, Rosen D, Kumagai Y. Significant, sustained improvement in knee function after intra-articular TPX-100: A double-blind, randomized, multi-center, placebo-controlled Phase 2 trial. *Arthr Rheum.* 2017; 69(10):13L McGuire D, Segal N, Metyas S, Barthel H R, Miller M, Rosen D, Kumagai Y. Intra-articular TPX-100 in knee osteoarthritis: Robust functional response at 6 and 12 months is associated with increased tibiofemoral cartilage thickness. *Arthr Rheum.* 2018; 70(10):L16

McGuire D, Bowes M, Brett A, Segal N, Miller M, Rosen D, Kumagai Y. Intra-Articular TPX-100 significantly delays pathological bone shape change at 6 and 12 Months in moderate to severe Tibiofemoral OA. *ACR Conf* 2019; Abs 1303

McGuire D, Bowes M, Brett A, Miller M, Kumagai Y. Significant reduction in femoral bone shape change at 12 months after IA TPX-100 correlates with Tibiofemoral cartilage stabilization. *Osteo & Cart 2020 World Congress.* 2020; S37-S38

Middleton-Hardie C, Aberman H, Alliston T, Mortazavi A, Rosen D. AC-100 Promotes cartilage defect repair In Vivo and chondrocyte differentiation and function In vivo. *ORS* 2010

Morshed A, Abbas A B, Hu J, Xu H. Shedding new light on the role of $\alpha v \beta 3$ and $\alpha 5 \beta 1$ integrins in rheumatoid arthritis. *Molecules.* 2019:24; 1537

Murphy M, Cerhio K, Stoch S, Gottsdiener K, Wu M, Recker R. Effect of L-00845704, an $\alpha v \beta 3$ integrin antagonist, on markers of bone turnover and bone mineral density in postmenopausal osteoporotic women. *The J of Clin Endocrin & Meta.* 2005; 90(4):2022-2028

Nagel D, Khosla S, Sanyal A, Rosen D, Kumagai Y, Riggs L. A fragment of hypophosphatemic factor, MEPE, required inducible Cyclooxygenase-2 to exert potent anabolic effects on normal human marrow osteoblast precursors. *J of Cell Biochem.* 2004; 93:1107-1114

Neogi T, Bowes M, Niu J, De Souza K, Vincent G, Goggins J, Zhang Y, Felson D T. MRI-based three-dimensional bone shape of the knee predicts onset of knee osteoarthritis: Data from the Osteoarthritis Initiative. *Arthr Rheum.* 2013; 65(8):2048-2058

Nevitt M C, Zhang Y, Javaid M K, Neogi T, Curtis J R, Niu J, McCulloch C E, Segal N, Felson D T. High systemic bone mineral density increases the risk of incident knee OA and joint space narrowing, but not radiographic progression of existing knee OA: The MOST study. *Ann Rheum Dis.* 2010; 69(1):163-168

Niemeyer P, Pestka J M, Kreuz P C, Erggelet C, Schmal H, Suedkamp N P, Steinwachs M. Characteristic complications after autologous chondrocyte implantation for cartilage defects of the knee joint. *Am J Sports Med.* 2008; 36(11):2091-2099

Reginster J Y, Badurski J, Bellamy N, Bensen W, Chapurlat R, Chevalier X, Christiansen C, Genant H, Navarro F, Nasonov e, Sambrook P N, Spector T D, Cooper C. Efficacy and safety of strontium ranelate in the treatment of knee osteoarthritis: Results of a double-blind, randomized placebo-controlled trial. *Ann Rheum Dis.* 2013; 72:179-186

Reichenbach S, Guermazi A, Niu J, Neogi T, Hunter D J, Roemer F W, McLennan C E, Hernandez-Molina G, Felson D T. Prevalence of bone attrition on knee radiographs and MRI in a community-based cohort. *Oste Cart.* 2008; 16(9):1005-1010

Rosen D, Middleton-Hardie C, Aswani S, Lazarov M. AC-100, A synthetic fragment of MEPE, promotes bone formation and maturation in rodent and canine bone regeneration models. *ORS.* 2006: Oral and Poster Presentation.

Ross F, Chappel J, Alvarez J, Sander D, Butler W, Farach-Carson M, Mintz K, Gehron Robey P, Teitelbaum S, Cheresh D. Interactions between the bone matrix proteins Osteopontin and bone Sialoprotein and the osteoclast integrin $\alpha v \beta 3$ Potentiate bone resorption. *The J of Bio Chem.* 1993; 268 (13):9901-9907

Rys J, DuFort C, Monteiro D, Baird M, Oses-Prieto J, Chand S, Burlingame A, Davidson M, Alliston T. Discrete spatial organization TGF-$\beta$ receptors couples receptor multimerization and signaling to cellular tension. *eLife.* 2015; 4:1-20

Rys J, Monteiro D, Alliston T. Mechanobiology of TGF-$\beta$ Signaling in the Skeleton. *Matrix Bio.* 2016; 52-54:413-425

Six N, Septier D., Chaussain-Miller C, Blacher R, DenBesten P, Goldberg M. Dentonin, a MEPE fragment, initiates pulp-healing response to injury. *J Dent Res.* 2007; 86(8): 780-785

Su J, Chiou J, Tang C, Zhao M, Tsai C, Chen P, Chang Y, Chien M, Peng C, Hsiao M, Kuo M, Yen M. CYR61 regulates BMP-2-dependant osteoblast differentiation through the $\alpha v \beta 3$ integrin/integrin-linked Kinase/ERK pathway. *The J of Biological Chem.* 2010; 285(41):31325-31336

Thi M, Suadicani S, Schaffler M, Weinbaum S, Spray D. Mechanosensory response of osteocytes to physiological forces occur along processes and not cell body and require $\alpha v \beta 3$ integrin. *PNAS.* 2013; 10(52):21012-21017

Williams T, Holmes A, Waterton J, Maciewicz R, Hutchinson C, Moots R, Nash A, Taylor C. Anatomically corresponded regional analysis of cartilage in asymptomatic and osteoarthritic knees by statistical shape modelling of the bone. *IEEE Trans on Med Imaging.* 2010; 29(8):1541-1559

Wipff P, Hinz H. Integrins and the activation of latent transforming growth factor $\beta 1$—an intimate relationship. *Euro J of Cell Bio.* 2008:87; 601-615

Woolf A D, Pfleger B, Burden of major musculoskeletal conditions. *Bull of the World Health Org.* 2003; 81(9): 646-656

Wu M, Chen G, Li Y P. TGF-$\beta$ and BMP signaling in osteoblast, skeletal development, and bone formation, homeostasis and disease. *Bone Res.* 2016; 4:16009

Zaslav K, Cole B, Brewster R, DeBernardo T, Farr J, Fowler P, Nissen C. A prospective study of autologous chondrocyte implantation in subjects with failed prior treatment for articular cartilage defect of the knee: Results of the study of the treatment of articular repair (STAR) clinical trial. *Am J Sports Med.* 2009; 37:42-55

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of treatment, comprising:
injecting a patient with a composition comprising a pharmaceutically acceptable, injectable carrier, and a peptide after (a) testing and confirming the peptide binds integrin αVβ3 expressed by osteocytes, and (b) testing and confirming the peptide is agonistic on binding to integrin αVβ3 expressed by osteocytes, and is not antagonistic, inhibitory, or blocking and (c) testing and confirming that binding to integrin αVβ3 expressed by osteocytes is at a level so as to result in improving joint function upon injection into the patient;
measuring 3D bone shape change by obtaining a bone image and analyzing the image with an algorithm which calculates the 3D bone shape, and wherein the 3D bone shape is determined by a B-score;
wherein the peptide consists of the amino acid sequence of SEQ ID NO: 10.

2. The method of claim 1, whereby the injecting results in slowing a change of three-dimensional (3D) bone shape upon injection into the patient.

3. The method of claim 1, further comprising:
continuing the injecting at different points in time until the composition delays, arrests, or reverses 3D bone shape change in the patient.

4. The method of claim 3, wherein the 3D bone shape change occurs in a joint of the patient.

5. The method of claim 4, wherein the 3D bone shape change occurs in a knee joint.

6. The method of claim 3, wherein the 3D bone shape change in the joint is associated with natural aging.

7. The method of claim 3, wherein the 3D bone shape change in the joint is pathological.

8. The method of claim 3, wherein the 3D bone shape change in the joint is associated with one or more of osteoarthritis, rheumatoid arthritis, trauma, osteoporosis, disc herniation, spinal injury, or temporomandibular disorder; and wherein the 3D bone shape change occurs in one or more of the joints of knee, hip, ankle, toe, finger, hand, wrist, elbow, shoulder, spine, or jaw.

9. The method of claim 1, wherein the composition reduces a pathological event selected from the group consisting of excessive mineralization of the bone, and excessive bone sclerosis.

10. The method of claim 1, wherein the binding affinity of the peptide to integrin $\alpha_v\beta_3$ is at least 300 times higher than its binding affinity to the integrins $\alpha_v\beta_1$, $\alpha_v\beta_6$, $\alpha_v\beta_8$, $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_8\beta_1$, $\alpha_9\beta_1$, and $\alpha_{10}\beta_1$.

11. The method of claim 10, wherein the peptide also binds integrin $\alpha_v\beta_5$ with a lower affinity than the peptide's affinity to integrin $\alpha_v\beta_3$.

12. The method of claim 11, wherein the binding affinity of the peptide to integrin $\alpha_v\beta_3$ is at least three (3) times higher than its binding affinity to the integrin $\alpha_v\beta_5$.

13. A method of treatment, comprising:
injecting a patient with a composition comprising a pharmaceutically acceptable, injectable carrier, and a peptide after (a) testing and confirming the peptide binds integrin αVβ3 expressed by osteocytes, and (b) testing and confirming the peptide is agonistic on binding to integrin αVβ3 expressed by osteocytes, and is not antagonistic, inhibitory, or blocking and (c) testing and confirming that binding to integrin αVβ3 expressed by osteocytes is at a level so as to result in improving joint function upon injection into the patient;
wherein the peptide consists of the amino acids of SEQ ID No: 10
measuring 3D bone shape change by obtaining a bone image and analyzing the image with an algorithm which calculates the 3D bone shape.

14. The method of claim 13, wherein the bone image is obtained using imaging technology selected from the group consisting of magnetic resonance (MR), radiography (X-ray), computer tomography (CT) and ultrasound.

15. The method of claim 14, wherein the algorithm is based on active appearance modeling (AAM).

* * * * *